US011317869B2

(12) United States Patent
Aeschlimann et al.

(10) Patent No.: US 11,317,869 B2
(45) Date of Patent: May 3, 2022

(54) MEDICAL DEVICE, APPARATUS, AND SURGICAL METHOD

(71) Applicant: Woodwelding AG, Stansstad (CH)

(72) Inventors: Marcel Aeschlimann, Ligerz (CH); Jörg Mayer, Niederlenz (CH); Mario Weiss, Diessbach bei Buren (CH); Aymeric Niederhauser, Tramelan (CH)

(73) Assignee: WOODWELDING AG, Stansstad (CH)

( * ) Notice: Subject to any disclaimer, the term of this patent is extended or adjusted under 35 U.S.C. 154(b) by 515 days.

(21) Appl. No.: 15/516,210

(22) PCT Filed: Oct. 2, 2015

(86) PCT No.: PCT/CH2015/000150
§ 371 (c)(1),
(2) Date: Mar. 31, 2017

(87) PCT Pub. No.: WO2016/049789
PCT Pub. Date: Apr. 7, 2016

(65) Prior Publication Data
US 2018/0153474 A1    Jun. 7, 2018

(30) Foreign Application Priority Data

Oct. 3, 2014    (CH) ..................... 01509/14

(51) Int. Cl.
*A61B 5/00*  (2006.01)
*A61N 1/05*  (2006.01)
(Continued)

(52) U.S. Cl.
CPC .......... *A61B 5/6868* (2013.01); *A61B 5/0006* (2013.01); *A61B 5/291* (2021.01);
(Continued)

(58) Field of Classification Search
CPC ............ A61B 17/68; A61B 2560/0219; A61B 2560/063; A61B 2562/0209;
(Continued)

(56) References Cited

U.S. PATENT DOCUMENTS

| 2004/0138581 | A1  | 7/2004 | Frei et al. |
| 2005/0075680 | A1* | 4/2005 | Lowry ................. A61N 1/0531 607/45 |

(Continued)

FOREIGN PATENT DOCUMENTS

| EP | 2 063 793    | 4/2011 |
| JP | 2014-079387  | 5/2014 |

(Continued)

OTHER PUBLICATIONS

International Preliminary Report on Patentability dated Apr. 4, 2017, Application No. PCT/CH2015/000150, 12 pages.
(Continued)

*Primary Examiner* — Eun Hwa Kim
*Assistant Examiner* — Rachel A. Vierra
(74) *Attorney, Agent, or Firm* — Rankin, Hill & Clark LLP

(57) ABSTRACT

An EEG headpiece includes an array of electrode pins, each electrode pin extending between a proximal end, formed by a proximal end face, and a distal end and including a conducting electrode and a thermoplastic material. The thermoplastic material is arranged at least around a periphery of the electrode pin or is pressable from a hollow space to the periphery. Each electrode pin is equipped for the transmission of energy, especially mechanical vibration energy, from the proximal end face to the thermoplastic material to liquefy at least portions of the thermoplastic material from a solid state to a flowable state, whereby the thermoplastic material is capable of flowing into structures
(Continued)

of a tissue portion surrounding the periphery and of forming, after re-solidification of the thermoplastic material, an anchoring of the electrode pin in the tissue portion.

14 Claims, 12 Drawing Sheets

(51) Int. Cl.
*A61B 5/291* (2021.01)
*A61B 5/316* (2021.01)

(52) U.S. Cl.
CPC .............. *A61B 5/316* (2021.01); *A61B 5/686* (2013.01); *A61B 5/6865* (2013.01); *A61B 5/6882* (2013.01); *A61N 1/0534* (2013.01); *A61B 5/002* (2013.01); *A61B 2560/0219* (2013.01); *A61B 2560/063* (2013.01); *A61B 2562/0209* (2013.01); *A61B 2562/046* (2013.01); *A61N 1/0539* (2013.01)

(58) Field of Classification Search
CPC . A61B 2562/046; A61B 5/0006; A61B 5/002; A61B 5/04012; A61B 5/0478; A61B 5/1459; A61B 5/6839; A61B 5/686; A61B 5/6865; A61B 5/6868; A61B 5/6864; A61B 5/6878; A61L 31/048; A61L 31/06; A61M 37/00; A61M 37/0015; A61N 1/0502; A61N 1/0534; A61N 1/0539; A61N 2005/067; A61N 2007/0026; A61N 2/006; A61N 5/0622; A61N 7/02
See application file for complete search history.

(56) References Cited

U.S. PATENT DOCUMENTS

| | | | |
|---|---|---|---|
| 2006/0123917 A1 | 6/2006 | Kibblewhite | |
| 2007/0225695 A1* | 9/2007 | Mayer | A61B 18/22 606/15 |
| 2007/0265622 A1 | 11/2007 | Aeschlimann et al. | |
| 2008/0255582 A1* | 10/2008 | Harris | A61B 5/0478 606/129 |
| 2009/0118804 A1* | 5/2009 | Moffitt | A61N 1/0539 607/116 |
| 2011/0093008 A1* | 4/2011 | Mayer | A61B 5/4839 606/213 |
| 2011/0175568 A1* | 7/2011 | Leijssen | A61N 1/3787 320/108 |
| 2011/0257694 A1 | 10/2011 | Mayer et al. | |
| 2011/0273270 A1* | 11/2011 | Brumer | A61B 5/282 340/10.1 |
| 2012/0253105 A1* | 10/2012 | Mayer | H04R 25/606 600/25 |
| 2012/0302856 A1 | 11/2012 | Chang et al. | |

FOREIGN PATENT DOCUMENTS

| | | |
|---|---|---|
| WO | 02/069817 | 9/2002 |
| WO | 2004/017857 | 3/2004 |
| WO | 2005/105208 | 11/2005 |
| WO | 2008/034276 | 3/2008 |
| WO | 2008/128367 | 10/2008 |
| WO | 2011/029208 | 3/2011 |

OTHER PUBLICATIONS

English translation of Japanese Office Action dated Mar. 9, 2021, Application No. 2017-517644, 6 pages.

* cited by examiner

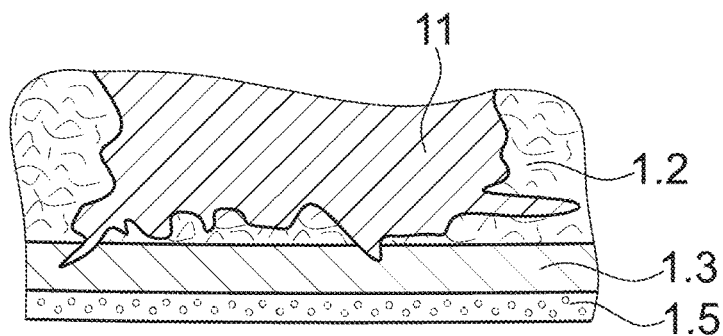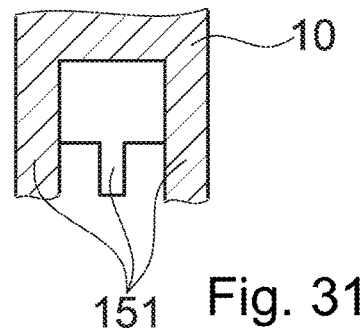
Fig. 30　Fig. 31
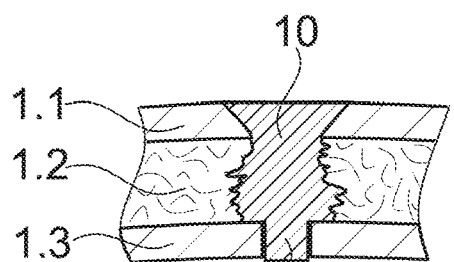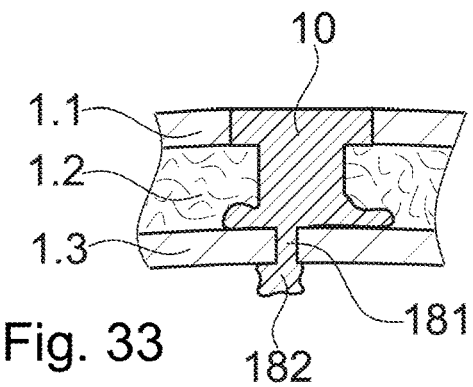
Fig. 32　Fig. 33
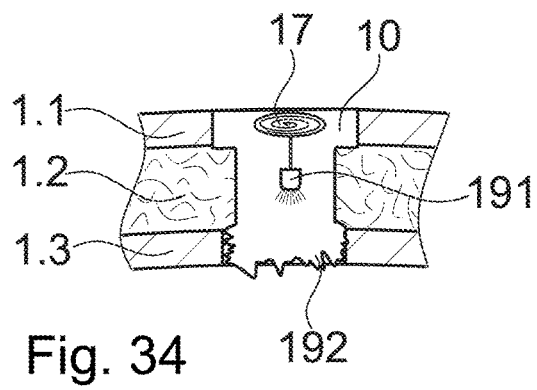
Fig. 34
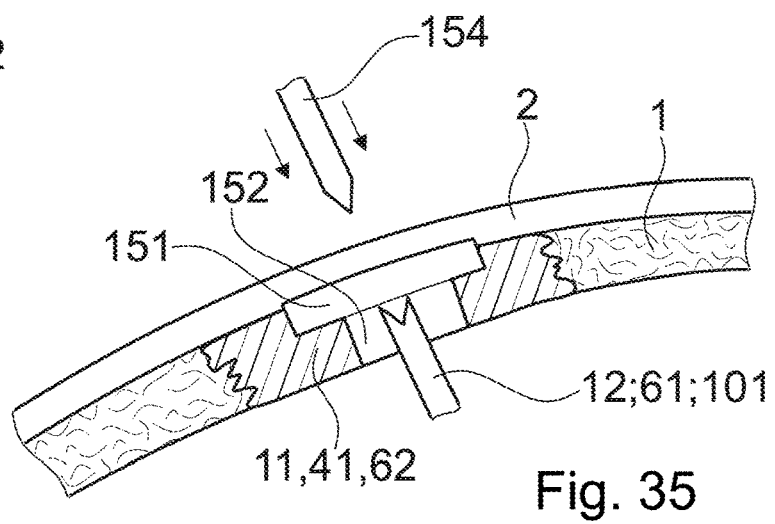
Fig. 35

MEDICAL DEVICE, APPARATUS, AND SURGICAL METHOD

BACKGROUND OF THE INVENTION

Field of the Invention

The invention is in the fields of medical technology and man-machine interaction. In particular, it relates to neuromodulation as well as diagnostics, monitoring, and stimulation of the human brain.

Description of Related Art

Electroencephalography as well as electrical stimulation of regions of the brain become increasingly important for many applications in diagnostics and therapeutics.

For example, for Parkinson patients and other movement disorders, deep brain stimulation (DBS) has been very effective. In DBS, an electrode is inserted into the brain and stimulates certain areas on the center of the brain. There has also been success with other therapies based on brain stimulation, including treatment of affective disorders.

Electroencephalography, i.e. the recording of electrical activity of the brain, has many diagnostic applications but is increasingly also used as part of treatments (for example for epileptics), or for making up for deficits. For example, there have been successes in controlling the movement of artificial limbs by way of human brain electric signals.

Both, electrical stimulation of the brain and electroencephalography (EEG) require electrodes sufficiently close to the brain.

According to a first approach according to the prior art, for electroencephalography, electrodes on the skull are used, which are brought in contact with the scalp. However, the signal transmission capacity both from the brain and to the brain is limited due to the fact that the signals have to travel through the scalp, the skull and the meninges and due to disturbances from the environment. Especially, the spatial resolution of signal recoding is limited, both for measuring and for inducing signals, due to the different tissues between the electrode and a local brain region. Additionally, some conductive gel has to be applied between the electrode and the skin to reduce the impedance.

Thus, in some cases the EEG gained from electrodes on the skull is not sufficient. Then, according to a second approach, for example for intracranial Electroencelography (Electrocorticography), subcranial, especially subdural electrodes are used. These intracranial or depth electrodes are more effective since they measure signals inside the skull. However, they are invasive, i.e. they require a surgery, where they are implanted, which is much more expensive and can lead to complications. Surgery is performed by temporarily removing a whole part of the cranial bone. This requires a burr hole in each corner of the opening and mechanic sawing to connect the holes or creation of a larger access hole through a trepanation procedure. A particular problem of intracranial electrodes is that they need to be contacted from an outside, and this causes a permanent risk of infections.

For deep brain stimulation electrodes implanted deep in the brain are necessary. These electrodes are implanted through drilled holes in the skull and, unlike subdural electrodes, do not require that the skull is opened. Therefore, their application is easier. However, they cause more discomfort for the patient. And even if they only require drill holes, their insertion is not necessarily quick, because the surgeon can only drill slowly in order to avoid that the bone gets too warm. Also, it has an infection rate of presumably about 6% and leads to intracranial bleeding for 2.0-2.5% of the implants.

It has also been proposed to implant devices that include electrodes, which devices include antennae for receiving power and signal from outside of the scalp by induction. However, also in these, the skull has to be opened for insertion.

SUMMARY OF THE INVENTION

It is an object of the present invention to overcome drawbacks of prior art approaches and to provide methods and devices suitable for sensing electrical signals from the brain or for delivering signals to the brain, for example for stimulation.

The invention firstly provides methods of implanting devices capable of transmitting an electrical signal (such as changes of the electrical potential over time or as a function of the position) to the central nervous system or of sensing an electrical signal emitted by the central nervous system are provided.

However, the invention also concerns implanting devices that include at least one of A micro drug or nutrient delivery system;
An actuator e.g. electro-magnetic or piezo-electric or pneumatic stimulator;
A sensor, for example to measure the intracranial pressure or brain temperature;
An ultrasonic sonotrode;
A piezo speaker;
An optical sensor, such as a camera, for optical analysis in the visible and/or near infrared part of the optical spectrum,
A light conducting or light emitting element, for example a laser diode, for example for therapy or the measurement of oxygenation, chemical analysis (metabolism analysis) in the cortex, especially in long term intensive care of brain trauma patients, wherein any one of these devices is implanted to be in physical contact with the brain or other parts of the nervous system or is otherwise placed to interact with the brain or other parts of the nervous system.

Arrays and/or combinations of these and/or of devices capable of transmitting an electrical signal to the central nervous system or of sensing an electrical signal emitted by the central nervous are possible.

In any aspect of the invention, the implantation method may include providing a fastening element—that may be an electrode/sensor/stimulator/delivery system carrier or a fastening element separate therefrom—that includes a thermoplastic material arranged at least on surface ranges of the fastening element or in a hollow space from which it can be pressed out through openings. Such a fastening element is equipped to be anchored in an object that includes structures into which the thermoplastic material is pressed in a liquid state so that after re-solidification it forms a positive-fit with the object. Such object may especially be bone tissue but can also be a dimensionally stable element of the device itself.

In this, at least portions of the thermoplastic material are liquefied in situ and pressed into the structures, thereby penetrating the object, by the joint action of energy and a pressing force. The energy may especially be mechanical vibration energy.

A first aspect of the invention concerns the application of an array (regular or irregular array) of sensing and/or delivery spots, for signal sensing or signal delivery or material (drug or nutrient or marker) delivery, to the central nervous system. An example of such an array is an array of EEG electrodes.

According to the first aspect of the invention, a sensing and/or delivery headpiece (such as an EEG headpiece) includes an array of interaction pins (for example electrode pins), each interaction pin extending between a proximal end, formed by a proximal end face, and a distal end and including an interaction element (such as an electrically conducting electrode) and a thermoplastic material. The thermoplastic material is arranged at least around a periphery of the interaction pin or is pressable from a hollow space to the periphery. Each interaction pin is equipped for the transmission of energy, especially mechanical vibration energy, from the proximal end face to the thermoplastic material to liquefy at least portions of the thermoplastic material from a solid state to a flowable state, whereby the thermoplastic material is capable of flowing into structures of a tissue portion surrounding the periphery and of forming, after re-solidification of the thermoplastic material, an anchoring of the interaction pin in the tissue portion.

The first aspect of the invention also concerns a method of implanting such a headpiece. This method may include pre-drilling a hole for each interaction pin and subsequently placing the pin and impinging it with energy such as mechanical vibration energy before and/or while it is pressed towards a distal direction, to liquefy at least portions of the thermoplastic material from a solid state to a flowable state, whereby the thermoplastic material is caused to flow into structures of a tissue portion surrounding the periphery and to thereby anchor, after re-solidification of the thermoplastic material, the interaction pin in the tissue portion. In embodiments with an interaction device—as described in more detail hereinbelow—the method further includes providing the interaction device.

Prior art EEG devices either include electrodes on the skull, with the discussed limits in spectral resolution (down to a few centimetres only) and sensitivity, or include electrode array carriers placed underneath the cranial bone or depth electrodes reaching inside the brain. In the latter case, a substantial portion of the cranial bone has to be removed to open the skull, whereby the implantation procedure is highly invasive. In contrast thereto, the approach according to the first aspect of the invention is only minimally invasive. Nevertheless it makes possible that the interaction elements can be very close to the brain and even in physical contact therewith if desired. The positions of the interaction elements along the skull can be almost arbitrarily chosen. Especially, compared to prior art intracranial EEG they are not restricted to a relatively small part of the brain but can be distributed over the whole skull.

Compared with non-invasive electrodes, these electrodes of this headpiece offer a much better signal quality. Without bone, skin and hair, there's much less signal noise and signal distortions that pose a problem for conventional non-invasive EEG applications, and the impedance is lower. Unlike these applications, the electrodes offer a signal recording below the skull bone (intracranial).

For EEG applications, where the interaction element is an electrode, the array may include any number of electrodes, distributed over a restricted part of the human head or over the entire head. The number of interaction pins in embodiments may be at least 6, at least 10, at least 15 or at least 25 or also more. Due to the fact that the electrodes are close to the brain, the spatial resolution is superior to the spatial resolution of classical EEG, so that it may make sense to place an even larger number of for example 50 or more interaction pins.

The electrode, if interaction element is an electrode, is especially arranged to reach the distal end or at least to close thereto (for example within 2 mm from it) of the interaction pin so that the brain signals are picked up from close thereto (or stimulation of the brain is carried out from close thereto). Such an arrangement at the distal end may be advantageous for other interaction elements, too.

The length of the interaction pin may be adapted to the thickness of the cranial bone. For adult patients, the length may be between 5 mm and 8 mm.

In accordance with a preferred embodiment, the thermoplastic material will be arranged so that in at least one depth (axial position) it forms the whole surface at least after the liquefaction, so that any functional part (for example the interaction element if it is separate from the thermoplastic material, if applicable possibly with wiring, control, mechanical carrier etc.) is embedded by the thermoplastic material or the thermoplastic material forms a sleeve or collar around it/them.

Because during the process the liquefied material is at an elevated temperature—and especially so where in contact with the tissue if the energy is mechanical energy —, this will also lead to sterility at the anchoring site. Further, due to intimate contact that includes the penetration also into the finest tissue structure a sealing effect that effectively keeps germs out of the intracranial region results. This sealing effect and configurations of thermoplastic material arranged on pins, especially for substance delivery, have been described in WO 2011/029208.

In embodiments of the first aspect, in addition or as an alternative to including electrodes for EEG or stimulation, the interaction element (for example functional core) could also be another functional part that is inserted into the head within the pin. Examples of interaction elements in this are:
  A micro drug or nutrient delivery system;
  An actuator e.g. electro-magnetic or piezo-electric or pneumatic stimulator;
  A sensor, for example to measure the intracranial pressure or brain temperature;
  An ultrasonic sonotrode;
  A piezo speaker;
  A camera, for optical analysis like near-infrared;
  A light conducting or light emitting element, for example a laser diode, for example for therapy or the measurement of oxygenation, chemical analysis (metabolism analysis) in the cortex, especially in long term intensive care of brain trauma patients.

Arrays with combinations of these elements (for example with some interaction pins that have an electrode, other interaction pins that have an actuator and/or for example at least one interaction pin with a light conducting or light emitting element) are possible.

Electro-magnetic or ultrasonic therapies (with ultrasonic arrays), as proposed here with functional pins, are already applied from outside the skull (the former is known as transcranial magnetic stimulation (TMS), the latter is called high intensity focused ultrasound (HIFU)). The ultrasound is however refracted by the cranial bone making complicated calculations necessary, which calculations can be dropped, if the functional element is applied below the skull or is part of the skull—i.e. being a part of the through-reaching pin having an effector at its distal end. Like the ultrasonic array, whose beams create a concentrated heat in a very specific area of the brain, also the sound waves from the piezo speaker can be concentrated if applied in an array and might be used for stimulation. For this, there exists the possibility of using interferences between sound waves acting from different positions, caused by different ones of the interaction elements.

Besides the medical use for diagnosis and treatment, the information gained from the mentioned sensorial applications can be used for a wide range of other applications like research, individual health monitoring, gaming, professional applications of thought control, automated surveillance of key professionals like pilots. As another example, epilepsy patients may have a few monitoring pins combined with a stimulator pin or for example additionally or as an alternative drug delivery pin that prevents seizures automatically.

The interaction pins of the headpiece may be physically connected for example by cabling, a flexible carrier or the like. Alternatively, they may be physically separate. Also if they are physically separate, they will be part of a functional unit in that they are communicatively connected to a control and/or evaluation unit.

The interaction pins may in accordance with a first possibility be physically contacted. It is already known from deep brain stimulation to guide such cabling subcutaneously from the head to an implanted pulse generator, for example implanted on the chest. Similarly, a central unit may be implanted and connected to the array of functional elements in embodiments of the present invention.

In accordance with a second possibility, the interaction pins may be such as to be buried underneath tissue, for example underneath the skin, and thus be fully inside the body, without a contact lead to an electronic unit. Especially, a purpose of the interaction pins may be to bridge the barrier constituted by the bone—especially the cranial bone—for the particular signal or substance to be sensed or delivered.

For electrical signals, for example for EEG or for stimulation, the cranial bone by being a dielectric (thereby being an electrostatic "resistor" reducing potential differences) of a certain thickness weakens the electrical field caused by potential differences in the brain or of stimulating electrodes. Further, the spatial resolution is reduced.

Similar considerations apply for ultrasonic waves, for example for ultrasonic imaging.

For optical signals, the cranial bone is substantially intransparent, and light coupled through it is dramatically weakened across the cranial bone.

For the delivery of substances, the cranial bone is substantially a barrier.

In accordance with the second possibility, the arrangement of the interaction pins forms a permanent array of bridges for the desired kind of interaction.

In accordance with a first group of embodiments implementing the second possibility, the interaction pins each include an interaction element in the form of a 'buried' electrode being an electrically conducting bridge between a proximal interaction point and a distal interaction point. By this, the electric potential at the proximal interaction point (at or close to the proximal end of the interaction pin and hence for example at or close to the outer surface of the cranial bone) is always equal to the electric potential at the distal interaction point (at or close to the distal end of the interaction pin, thus for example at or close to the inner surface of the cranial bone). The interaction element in this may, for example, be a simple electrically conducting bar or include a proximal and a distal interaction electrode, the interaction electrodes being conductively connected. Alternatively, the thermoplastic material of the interaction pin itself may be the interaction element/electrically conducting bridge by being made of an electrically conductive thermoplastic material. Such electrically conductive material may for example include a polymer matrix with a sufficient concentration an electrically conductive filler.

In accordance with a second group of embodiments, the interaction pins may consist of transparent material (in which case the thermoplastic material itself constitutes the interaction element) or include a core of a transparent material so that the optical barrier constituted by the cranial bone is bridged.

In accordance with an even further, third group of embodiments, the interaction pin may include a material with a resistance to acoustical waves that is substantially below the according resistance of the cranial bone. For example, the acoustic impedance of the interaction element may be approximately matched to the acoustic impedance of brain tissue at frequencies usual for diagnostic ultrasonic imaging, so that the vibrations can effectively be coupled into the brain tissue and back.

As an even further group of embodiments, the interaction pin may include an interaction element being in the form of a channel for a substance thus effectively forming an access port to the central nervous system.

As a third possibility, the interaction pins may be contacted wirelessly, in accordance with the fourth aspect of the invention described in more detail hereinafter.

In accordance with any one of the three possibilities, the signal damping effect of the cranial bone may be bridged by the interaction pins. In embodiments according to a first configuration, to this end the cranial bone is broken through completely, i.e. perforated. The distal end of the interaction element may then be approximately flush with the distal surface of the cranial bone or protrude from it distally. In embodiments, the interaction element also pierces the meninges and is lead into the brain (see the third aspect described hereinbelow).

In embodiments according to a second configuration, the cranial bone is not completely bridged, but a portion, especially an interior (distal) bone lamella is kept intact. This features the advantage that the risk of infections and generally the surgical risk is drastically reduced. Especially, the interior cortical bone portion may be left intact. In embodiments, it may even during the anchoring serve as abutment portion, especially if the interaction pin is suitable shaped by having a delicate structure of not too strong/stiff portions, for example distal feet. Then, the anchoring process will cause some spreading of the thermoplastic material on the proximal side of the interior cortical bone. If for example, according to the above-mentioned option, the thermoplastic material is itself conducting and forms the interaction element or a part thereof, this will enhance the effectivity.

More in general, an advantage of the second configuration is that the thermoplastic material of the interaction pin will be caused to become soft by the effect of the energy and will adapt locally and individually to the strongly varying thickness of the cranial bone without there being a risk of penetrating the interior lamella.

Because the interior-most bone lamella, although it is formed of dense cortical bone, will have a rather good electrical conductivity due to the fact that it is covered by a periosteum that is intensely supplied with blood. Thus, the additional electrical field resistance due to this lamella is rather small compared to solutions that pierce the cranial bone completely.

Similarly, in optical applications, such a distal portion of the thermoplastic material that has interpenetrated the spongy bone tissue proximally of the interior cortical bone tissue, will by its attained shape, form a light diffusor if the thermoplastic material is sufficiently transparent. This principle of making a light diffusor by causing thermoplastic material to interpenetrate bone tissue has been described in WO 2005/105 208. Concerning the principle of the light diffusor obtained by this method, the present text refers to the teaching of WO 2005/105 208. In brain therapy, the coupling of light (visible light/infrared radiation or possibly UV radiation) into the tissue may by itself and/or together with an applied photoactivatable substance have a therapeutic effect. The coupling of light into the tissue may also be suitable for diagnostic purposes.

A further, rather general advantage of the second configuration is that the interior periosteum is left intact, and thus there is a reduced risk of the distal end of the interaction pin being overgrown by tissue (that will have a shielding effect) in a healing process.

In accordance with a variant of the first configuration (including perforating the cranial bone), like in the second configuration only a blind hole is made in the cranial bone, but from the blind hole a small perforation (micro-perforation) is made in the interior-most bone lamella. Thereby, a small droplet of liquefied material will enter into the cranial cavity and solidify there. Such droplet may, depending on the purpose and the properties of its material, serve as electrode, or as light bulb. Because of the very small dimension of such a micro-perforation and because of the fact that its surrounding will be sterilized by the effect of the liquefied thermoplastic material, also in this variant the risk of infections is very small.

The sensing and/or delivery headpiece may further include an interaction device adapted to the array of interaction pins.

For example, if the interaction pins are physically contactable according to the first possibility, the interaction device may have a number of contacts corresponding to the number of interaction pins, the contacts adapted to the interaction pins. For example, the interaction device may have an according number of plugs forming the contacts.

If the interaction pins are such that, according to the second or third possibility, not to be contacted physically, the interaction device may have an array of device interaction points adapted to the array. In an example, if the array of interaction pins is implanted in the cranial bone, the interaction device may include a cap to be carried by the user, the cap being adapted to the user and having an array of interaction electrodes defining the device interaction points, each interaction electrode located at the place of one of the interaction elements. Such interacting electrodes may, in embodiments, be similar to conventional EEG electrodes but in contrast to those benefit from the advantages of the array of interaction pins. It is also possible that the interaction device has a number of interaction electrodes (that again in embodiments may be similar to conventional EEG electrodes) that each are secured to a corresponding cable, whereby the electrodes may be placed at the locations of the interaction elements one by one by the operator.

In another example, if the interaction pins are implanted to connect the interior of the ear canal with an interior of the skull, the interaction device may include an earpiece, similar to the earpiece of a hearing aid, with the interaction points arranged appropriately on its surface. The interaction device may then even be integrated in a hearing aid.

A particular advantage of implantation from the ear canal is that it becomes possible to get close to the brain stem and deeper brain regions, on the one hand, and on the other hand the possibility of combinations with reference electrodes at the skullcap (calvarium) to measure transcranial potential differences, as explained in more detail hereinafter referring to Figures.

The interaction device may include a device control with signal processing means so that the interaction points may be controlled from the interaction device. Then, the interface to external devices may be generic. Alternatively, the interface may include a data and/or power lead for every interaction point, so that the control may be carried out from a separate, external device.

For designing the interaction device firstly the interaction pins may be set and then their position measured, and the interaction device may be tailor-made to fit the position of the interaction pins. To this end, a carrier carrying the elements (such as device interaction electrodes) constituting the interaction points may be provided. The carrier may have the shape of the part of the head to which the headpiece is applied. It may include a cap, an earpiece, or have any other suitable shape. It may be flexible or stiff, for example custom-made by CAD/CAM or additive manufacturing.

In special embodiments, there may be a plurality of spatially separated interaction elements in at least one of the interaction pins. For example, the interaction pin may include a small arrangement of for example two, three, four, more than four, . . . electrodes.

A set for carrying out the invention according to its first aspect may include in addition to the array of interaction pins and, if applicable, the interaction device, also at least one of the following:
   A template for defining the positions of the interaction pins;
   Software for an external device, the software cooperating with the interaction device to read out signals from the interaction elements and/or to deliver signals/material by the interaction elements, as well as a user interface;
   Information teaching the user to implant the array in the manner described in this text and/or at locations described in this text.

According to a second aspect of the invention, a method of implanting a generally flat electrode carrier (electrode carrier sheet) underneath the cranial bone and an according device are provided. The electrode carrier, for example, includes a plurality of electrodes, for example arranged in an array. The electrodes are appropriately contacted. The method includes providing a through opening in the skull, the through opening having an area that is smaller than an area of the electrode carrier. Especially, the opening may be a slit-like opening with a lateral extension being slightly larger than one of the lateral extensions of the electrode carrier but with a width being significantly smaller than the other lateral extension of the electrode carrier. The method further includes inserting the electrode carrier through the through opening until the electrode carrier lies flat between the brain and the cranial bone, essentially parallel to the meninges (on the meninges, or possibly between layers of the meninges). Thereafter, the method includes fixing the electrode carrier relative to the cranial bone with the aid of thermoplastic material and energy that causes the thermoplastic material to liquefy, from a solid to a liquid state, wherein the liquefied thermoplastic material is caused to penetrate into structures, especially of the cranial bone, so that after re-solidification it forms a positive-fit connection with the cranial bone tissue.

For the fixation of the electrode carrier to the tissue, one or more of the following possibilities may be used:

The device may include a fastening portion physically connected to the electrode carrier, which fastening portion includes a thermoplastic material and is equipped for being anchored in bone tissue of the cranial bone by being subject to energy, especially mechanical vibration energy while and/or before it is pressed against the tissue, so that the thermoplastic material is liquefied and after re-solidification forms an anchoring as well as a tight seal.

The device may include a fastening element initially separate from the electrode carrier and reaching through the cranial bone, with a distal end of the fastening element being equipped for mechanical coupling to the electrode carrier.

The device may include a separate fastening element with thermoplastic material, and the electrode carrier may include a fastening portion of a non-liquefiable material with a structure that is suitable to form a positive-fit connection with the thermoplastic material of the fastening element. The fastening element may in accordance with this possibility be pushed between the bone tissue and the structure to fasten them to each other and at the same time to provide a seal. Such fixation is, for example, described in EP 2 063 793 B1.

The electrode carrier may include an anchor that includes thermoplastic material or a thermoplastic portion and is fastened to the inner side of the cranial bone by means of a tool inserted through the slit-like opening by which tool energy, for example mechanical vibration energy, and a pressing force directed towards an outside are applied.

According to a possibility, the slit-like opening is cut by ultrasonic cutting. Ultrasound tools can have any shape and are not restricted to circular shapes. Furthermore ultrasonic cutting has the huge advantage that it only cuts solid materials, like the bone. Soft parts, like the dura or the brain are not hurt by the tool vibrating in ultrasound frequency. Today's burr hole drillers have a special functionality to avoid that soft parts get hurt. With ultrasound these expensive techniques are no longer necessary.

The electrodes of the electrode carrier may, for example, each be contacted by a conductor path of the electrode carrier, the conductor paths being contactable through the opening from an outside or leading to a processor element that is capable of at least one of storing, processing or having read out signals sensed by the electrodes. Especially, reading out can be accomplished by the approach according to the fourth aspect of the invention.

According to a third aspect, a device and method for implanting an interaction element, such as DBS electrode, deep in the human brain is provided, the method including
providing a deep brain interaction element carrier—that will, for example, be straight, thin needle-like pin —;
inserting the interaction element carrier until the interaction element has reached a desired position;
and using a process that includes the sub-steps of:
liquefying thermoplastic material of an anchoring and/or fixation element,
and causing thereby liquefied thermoplastic material to flow and thereafter to re-solidify,
for fixing a position of the interaction element carrier, being in the desired position, relative to the skull.

In this, in the step of inserting the interaction element carrier until the interaction element has reached a desired position may include obtaining a feedback about the actual position, for example by an imaging method, by an external positioning means such as a positioning frame, and/or by observing a reaction of the patient.

An advantage of this fixation method is that the implant fixation can be made very thin. A thin fixation reduces the exposure of the implant to the risk of unintended manipulation from the outside.

For fixing a position of the interaction element carrier relative to the skull, especially an anchoring body may be used.

Then, the step of fixing a position of the interaction element carrier may include fixing a position of the interaction element carrier relative to the anchoring body and/or fixing a position of the anchoring body, which guides the interaction element carrier, relative to the cranial tissue.

Such an anchoring body may according to a first example be implanted subcranially through a slit-like opening of the cranial bone prior to insertion of the interaction element carrier. When the interaction element carrier has been inserted, it is guided by the anchoring body.

According to a second example, an anchoring body may be implanted on the outside of the cranial bone. A fixation anchor including thermoplastic material may be used for fixing the interaction element carrier relative to the anchoring body.

A device according to the third aspect includes an interaction element carrier with at least one interaction element, the interaction element carrier being configured to be introduced from outside of the skull to penetrate into the brain, an anchoring body separate from the interaction element carrier, the anchoring body being configured to be fastened to the cranial bone, and at least one anchoring element or fixation element, the anchoring element or fixation element including thermoplastic material and being configured for at least one of:
being anchored in the cranial bone tissue by liquefying at least a portion of the thermoplastic material, causing thereby liquefied thermoplastic material to flow into structures of the cranial bone tissue and to yield, after re-solidification, an anchor;
fixing the interaction element carrier relative to the anchoring body by a process that includes liquefying thermoplastic material of an anchoring and/or fixation element, and causing thereby liquefied thermoplastic material to flow into structures of at the interaction element carrier or the anchoring body or both and thereafter to re-solidify.

According to a fourth aspect that can be combined with the first, second or possibly also the third aspect of the invention, a sensing and/or delivery installation (such as an EEG electrode implant) is provided, the installation including at least one interaction element (for example, electrode) for signal sensing or signal delivery or material (drug or nutrient or marker) delivery, wherein the installation further includes a processor unit communicatively coupled to the interaction element, wherein the installation is equipped for a wireless communication (that may include activation) and/or wireless energy transmission between the processor unit and a further unit. Moreover, at least one element the installation is equipped for being fastened to bone tissue with the aid of thermoplastic material that is liquefied for interpenetrating structures and re-solidified.

In this, the bone tissue to which the implant can be fastened may be cranial bone tissue, or tissue of the spinal cord. Alternatively, the bone to which the implant is fastened may be another bone, such as a rib, the clavicle, or any other bone. For example, fastening an interaction element on an inside of a rib may be used for surveillance of the functions of the heart and/or lung. Generally, the skeleton provides excellent reference points for sensing or delivering signals or delivering a substance.

The installation may include an implant that includes the interaction element and the processor element and that itself is equipped for wireless communication and/or wireless energy transmission between the processor unit and a further unit, and wherein the implant is equipped for being fastened to bone tissue with the aid of thermoplastic material that is liquefied for interpenetrating structures and re-solidified.

The processor unit may especially include an analog-to-digital converter (A/D converter). This features the advantage that digital signals are easier to read out.

The implant for the wireless communication may include an antenna.

If the interaction element is an electrode for sensing applications (such as EEG), the processor unit may be such as to de-couple the antenna from the electrode, especially so that a signal picked up by the antenna does not have any influence on the electrode voltage. Such an antenna may be integrated in the processor unit or be separate therefrom.

In embodiments, the implant includes a distal shaft portion and a proximal head portion, the head portion being wider than the shaft portion. The antenna in this may be located in the head portion so that the active area of the antenna is large compared to the dimensions of the shaft portion. The processor unit may be in the head portion and/or the shaft portion, and the interaction element will be located such as to reach to the distal end of the shaft portion or at least close thereto.

Especially, the processor unit may be equipped for RFID communication, especially, together with the antenna, as passive RFID transponder.

In addition or as an alternative to including an implant of the described kind, the installation may include a (separate) transmitter unit with an antenna. This transmitter unit may be equipped for being fastened to bone tissue with the aid of thermoplastic material that is liquefied for interpenetrating structures and re-solidified, for example by fasteners separate from the transmitter unit or one-piece with it.

The invention also concerns a method of implanting a sensing and/or delivery installation according to the fourth aspect, by means of the liquefiable material and energy and a pressing force impinging on it.

Many embodiments of the aspects of the invention include coupling mechanical vibration energy into the implanted devices for liquefying the thermoplastic material that anchors the devices or parts thereof. Mechanical vibration or oscillation suitable for devices and methods according to embodiments of the invention that include liquefaction of a polymer by friction heat created through the mechanical vibration has preferably a frequency between 2 and 200 kHz (even more preferably between 10 and 100 kHz, or between 20 and 40 kHz) and a vibration energy of 0.2 to 20 W per square millimeter of active surface. The vibrating element (sonotrode) is e.g. designed such that its contact face oscillates predominantly in the direction of the element axis (longitudinal vibration) and with an amplitude of between 1 and 100 µm, preferably around 10 to 30 µm. Rotational or radial oscillation is possible also.

For specific embodiments of devices, it is possible also to use, instead of mechanical vibration, a rotational movement for creating the named friction heat needed for the liquefaction of the anchoring material. Such rotational movement has preferably a speed in the range of 10,000 to 100,000 rpm.

A further way for producing the thermal energy for the desired liquefaction includes coupling electromagnetic radiation into one of the device parts to be implanted and designing one of the device parts to be capable of absorbing the electromagnetic radiation, wherein such absorption preferably takes place within the anchoring material to be liquefied or in the immediate vicinity thereof. Preferably electromagnetic radiation in the visible or infrared frequency range is used, wherein the preferred radiation source is a corresponding laser. Electric heating of one of the device parts may also be possible.

In this text the expression "thermoplastic material" (or "liquefiable material") refers to a material having thermoplastic properties. This includes thermoplastic polymers and thermoplastic polymers with added components, for example a filler of a material that itself would not have thermoplastic properties. "Thermoplastic material" is thus used for describing a material including at least one thermoplastic component, which material becomes liquid or flowable when heated, in particular when heated through friction i.e. when arranged at one of a pair of surfaces (contact faces) being in contact with each other and vibrationally or rotationally moved relative to each other, wherein the frequency of the vibration is between 2 kHz and 200 kHz, preferably 20 to 40 kHz and the amplitude between 1 µm and 100 µm, preferably around 10 to 30 µm. Such vibrations are e.g. produced by ultrasonic devices as e.g. known for dental applications or for CMF osteosynthesis applications for example in the SonicWeld RX® system by the KLSmartin group. For being able to constitute a load-bearing connection to the tissue, the material has an elasticity coefficient of more than 0.5 GPa, preferably more than 1 GPa. The elasticity coefficient of at least 0.5 GPa also ensures that the liquefiable material is capable of transmitting the ultrasonic oscillation with such little damping that inner liquefaction and thus destabilization of the liquefiable element does not occur, i.e. liquefaction occurs only where the liquefiable material is at the liquefaction interface to the stop face. The plastification temperature is preferably of up to 200° C., between 200° C. and 300° C. or even more than 300° C.

Depending on the requirements (for example, whether the anchoring by the thermoplastic material is to be slowly replaced by bone ingrowth), the liquefiable thermoplastic material may or may not be resorbable.

Suitable resorbable polymers are e.g. based on lactic acid and/or glycolic acid (PLA, PLLA, PGA, PLGA etc.) or polyhydroxyalkanoates (PHA), polycaprolactones (PCL), polysaccharides, polydioxanones (PD), polyanhydrides, polypeptides or corresponding copolymers or blended polymers or composite materials containing the mentioned polymers as components are suitable as resorbable liquefiable materials. Thermoplastics such as for example polyolefins, polyacrylates, polymetacrylates, polycarbonates, polyamides, polyesters, polyurethanes, polysulphones, polyaryl ketones, polyimides, polyphenyl sulphides or liquid crystal polymers (LCPS), polyacetals, halogenated polymers, in particular halogenated polyoelefins, polyphenylene sulphides, polysulphones, polyethers, polypropylene (PP), or corresponding copolymers or blended polymers or composite materials containing the mentioned polymers as components are suitable as non-resorbable polymers. Examples of suited thermoplastic material include any one of the polylactide products LR706 (amorphous Poly-L-DL lactide 70/30), L209 or L210S by Boehringer Ingelheim.

Specific embodiments of degradable materials are Polylactides like LR706 PLDLLA 70/30, R208 PLDLA 50/50, L210S, and PLLA 100% L, all of Boehringer. A list of suitable degradable polymer materials can also be found in: Erich Wintermantel und Suk-Woo Haa, "Medizinaltechnik mit biokompatiblen Materialien und Verfahren", 3. Auflage, Springer, Berlin 2002 (in the following referred to as "Wintermantel"), page 200; for information on PGA and PLA see pages 202 ff., on PCL see page 207, on PHB/PHV copolymers page 206; on polydioxanone PDS page 209. Discussion of a further bioresorbable material can for example be found in C A Bailey et al., J Hand Surg [Br] 2006 April; 31(2):208-12.

Specific embodiments of non-degradable materials are: Polyetherketone (PEEK Optima, Grades 450 and 150, Invibio Ltd), Polyetherimide, Polyamide 12, Polyamide 11, Polyamide 6, Polyamide 66, Polycarbonate, Polymethylmethacrylate, Polyoxymethylene, or polycarbonateurethane (in particular Bionate® by DSM, especially Bionate 75D and Bionate 65D; according information is available on datasheets publicly accessible for example via matweb.com by Automation Creations, Inc.). An overview table of polymers and applications is listed in Wintermantel, page 150; specific examples can be found in Wintermantel page 161 ff. (PE, Hostalen Gur 812, Höchst AG), pages 164 ff. (PET) 169 ff. (PA, namely PA 6 and PA 66), 171 ff. (PTFE), 173 ff. (PMMA), 180 (PUR, see table), 186 ff. (PEEK), 189 ff. (PSU), 191 ff. (POM—Polyacetal, tradenames Delrin, Tenac, has also been used in endoprostheses by Protec).

The liquefiable material having thermoplastic properties may contain foreign phases or compounds serving further functions. In particular, the thermoplastic material may be strengthened by admixed fillers, for example particulate fillers that may have a therapeutic or other desired effect. The thermoplastic material may also contain components that expand or dissolve (create pores) in situ (e.g. polyesters, polysaccharides, hydrogels, sodium phosphates) or compounds to be released in situ and having a therapeutic effect, e.g. promotion of healing and regeneration (e.g. growth factors, antibiotics, inflammation inhibitors or buffers such as sodium phosphate or calcium carbonate against adverse effects of acidic decomposition). If the thermoplastic material is resorbable, release of such compounds is delayed.

If the liquefiable material is to be liquefied not with the aid of vibrational energy but with the aid of electromagnetic radiation, it may locally contain compounds (particulate or molecular), which are capable of absorbing such radiation of a specific frequency range (in particular of the visible or infrared frequency range), e.g. calcium phosphates, calcium carbonates, sodium phosphates, titanium oxide, mica, saturated fatty acids, polysaccharides, glucose or mixtures thereof.

Fillers used may include degradable, osseostimulative fillers to be used in degradable polymers, including: β-Tricalciumphosphate (TCP), Hydroxyapatite (HA, <90% crystallinity; or mixtures of TCP, HA, DHCP, Bioglasses (see Wintermantel). Osseointegration stimulating fillers that are only partially or hardly degradable, for non degradable polymers include: Bioglasses, Hydroxyapatite (>90% cristallinity), HAPEX®, see S M Rea et al., J Mater Sci Mater Med. 2004 September; 15(9):997-1005; for hydroxyapatite see also L. Fang et al., Biomaterials 2006 July; 27(20):3701-7, M. Huang et al., J Mater Sci Mater Med 2003 July; 14(7):655-60, and W. Bonfield and E. Tanner, Materials World 1997 January; 5 no. 1:18-20. Embodiments of bioactive fillers and their discussion can for example be found in X. Huang and X. Miao, J Biomater App. 2007 April; 21(4):351-74), J A Juhasz et al. Biomaterials, 2004 March; 25(6):949-55. Particulate filler types include: coarse type: 5-20 μm (contents, preferentially 10-25% by volume), submicron (nanofillers as from precipitation, preferentially plate like aspect ratio >10, 10-50 nm, contents 0.5 to 5% by volume).

Filler materials that have the function of making the thermoplastic material electrically conductive, as described hereinbefore, are ideally provided with a filling degree sufficient for them to percolate, i.e. to form particle-particle contacts. Such filler particles may be metal fibers, whiskers or platelets (gold, platinum, etc), graphite platelets, carbon nanotubes, etc. It is also feasible that the thermoplastic material has a heterogeneous composition, for example with a high filling grade in a central region to yield a proximo-distal conducting bridge and a mantle region with a different filling grade and/or with a different filler optimized for other properties, such as flow properties to optimize the flow induced positive-fit and/or osseointegration properties. Especially, such a mantle region may be filled by CaP or another filler promoting osseointegration.

A specific example of a material with which experiments were performed was PLDLA 70/30 including 30% (weight percent) biphase Ca phosphate that showed a particularly advantageous liquefaction behaviour.

The materials of the functional core parts may be any materials that do not melt at the melting temperatures of the thermoplastic material, for example a metal. Preferred material for electrodes are Gold, Titanium, and Carbon.

The embodiments described in this text mainly focus on electrodes as interaction elements, and on embodiments where each interaction pin only carries one electrode and each element carrier only carries electrodes. However, it would also be possible to provide interaction pins/element carriers with multiple interaction elements and/or interaction pins/element carriers with different kinds of interaction elements.

BRIEF DESCRIPTION OF THE DRAWINGS

In the following, ways to carry out the invention and embodiments are described referring to drawings. The drawings are all schematical and not to scale. In the drawings, same reference numerals refer to same or analogous elements. The drawings show:

FIG. 30 a distal end of an interaction pin if the cranial bone is not pierced;

FIG. 31 a further embodiment of an interaction pin;

FIG. 32 another configuration of an interaction pin implanted in the cranial bone;

FIG. 33 and even further configuration of an interaction pin implanted in the cranial bone;

FIG. 34 an even further embodiment of an interaction pin;

FIG. 35 an access port;

DESCRIPTION OF THE PREFERRED EMBODIMENTS

Figure 1:
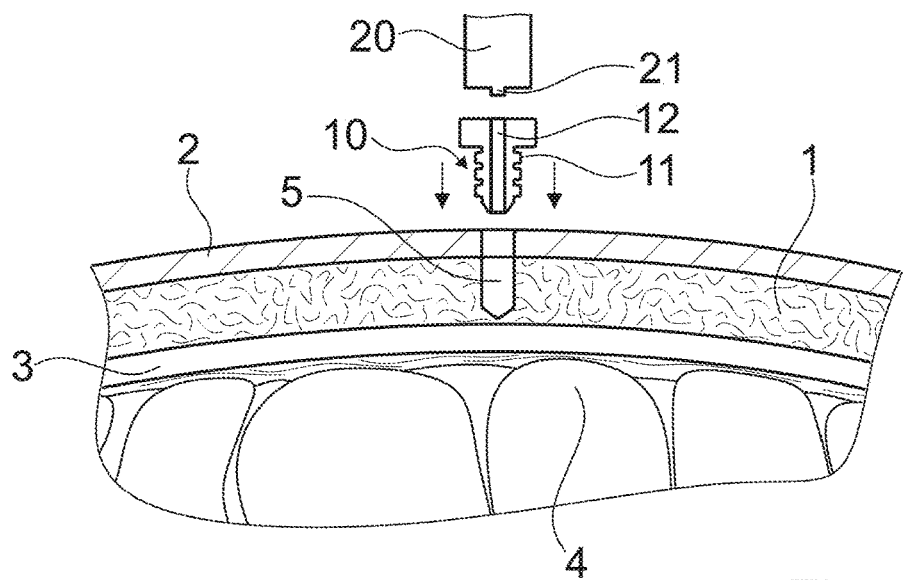
FIGS. 1 and 2 a section through a part of a human skull with an interaction pin; before and after implantation thereof.

FIG. 1 very schematically shows a cranial bone 1 with a scalp 2, and underneath the scalp the meninges 3 and the brain 4. An interaction pin 10 of an EEG headpiece is inserted into a pre-made bore 5. The interaction pin includes an electrode 12 that in the depicted version is shown to be through-going reaching from a distal end to the proximal end.

The length of the interaction pin 10 may be chosen such that it reaches essentially through the entire cranial bone of an adult patient, for example by having a length between 5 mm and 8 mm, especially at about 7 mm. Especially, the interaction pin 10 may have a length that causes it the distal end of the electrode 12 to be essentially level with the inner surface of the cranial bone or slightly distally thereof but that does not cause it to penetrate the Dura of the meninges.

The electrode is surrounded by a thermoplastic portion 11 of the interaction pin 10. The thermoplastic portion is especially arranged such that it completely surrounds the functional core (that includes the electrode or is connected thereto) in at least one axial (proximodistal) position such that it surrounds the functional core by embedding it or at least by forming a collar around it.

For anchoring of the interaction pin in the cranial bone, the anchoring pin is inserted in the bore 5 and pressed towards a distal direction while and/or after mechanical vibration energy is coupled into it by an appropriate tool, especially a sonotrode 20. To this end, the sonotrode 20 is pressed against a proximal coupling face formed by the proximally facing end of the interaction pin 10. The proximal end of the interaction pin may optionally include an axial recess or other structure cooperating with a correspondingly mating structure 21 of the sonotrode to guide the pin and the sonotrode relative to one another during insertion.

The step of coupling energy into the interaction pin 11 and applying vibration is carried out until by the effect of the pressing force and the mechanical vibration, due to external and internal friction in the thermoplastic material, the thermoplastic material at least in the periphery becomes flowable and is pressed into structures of the cranial bone tissue. This will lead to an anchoring of the interaction pin in the tissue after re-solidification of the thermoplastic material in a positive-fit manner.

Figure 2:
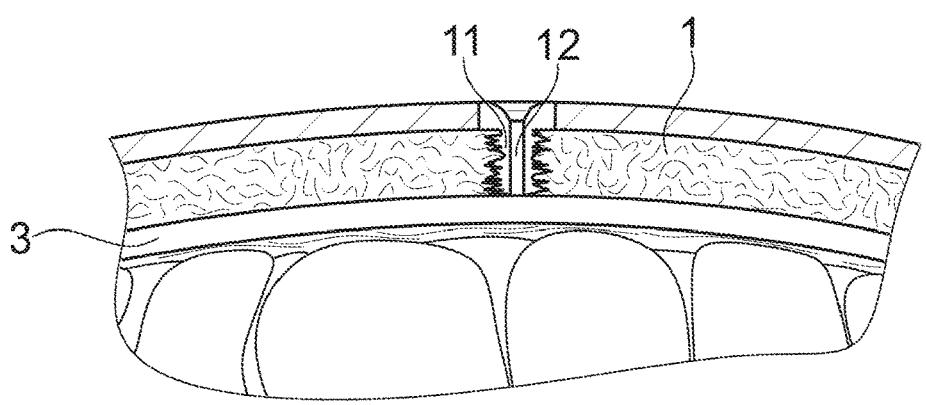

As illustrated in FIG. 2, this anchoring process results in material of the thermoplastic portion 11 penetrating the bone tissue. As explained in more detail hereinafter, the cranial bone is a flat bone with a spongy (cancellous) bone sandwiched between two comparably thin layers of compact (cortical) bone. The cranial bone is on both sides covered by periosteum. The anchoring process provides an especially efficient fixation in the spongy bone because interpenetration of the spongy bone tissue by the liquefied and re-solidified thermoplastic material. Because during the process the liquefied material is at an elevated temperature, this will also lead to improved sterility at the anchoring site. Further, due to intimate contact that includes the penetration also into the finest tissue structure, a sealing effect that effectively keeps germs out of the intracranial region results.

In the embodiment of FIGS. 1 and 2, the electrode 12 is depicted to be physically contactable from the proximal end, so that, for example, a wire can be connected to it. Such a wire may be arranged to lead directly through the scalp to contact the electrode from outside of the skull or may be arranged subcutaneously to be contacted by an appropriate implanted device, for example at a periphery of the skull or on the chest or at another place.

As an alternative to being physically contactable, the interaction pin may also be equipped to be contacted wirelessly, by electromagnetic fields, for example by electromagnetic induction and/or electromagnetic waves, especially by RFID.

Figure 3:
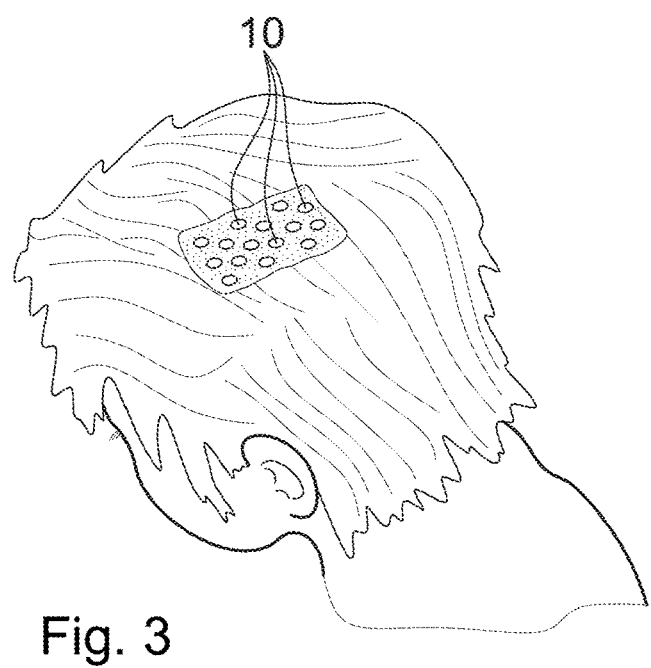
FIG. 3 a skull with a headpiece including an array of interaction pins.

FIG. 3 depicts an array of interaction pins 10 implanted in a skull. In practice, such an array may include any number of electrodes, distributed over a restricted part of the human head or over the entire head. The number of interaction pins in embodiments may be at least 6, at least 10, at least 15 or at least 25 or also more. Despite the potentially large number of electrodes, the implantation is little invasive, quick and straightforward, with minimal risk of infection.

Figure 4:
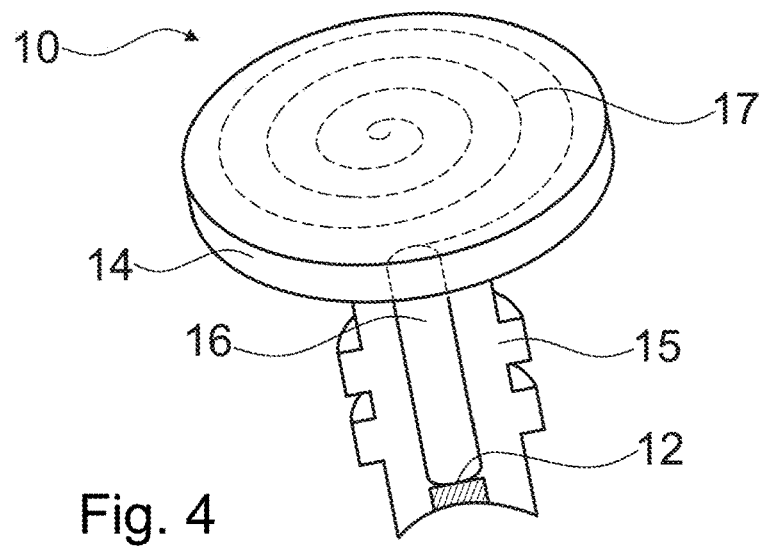
FIG. 4 a variant of an interaction pin with RFID chip and antenna.

FIG. 4 yet shows an interaction pin 10 that is equipped for being contacted wirelessly. The interaction pin 10 includes a head portion 14 and a shaft portion 15. For wireless communication and also for being powered from externally, the interaction pin in the head portion includes a processor unit 16, namely an RFID chip, and an antenna 17. The antenna is arranged in the head portion 14 to maximize its active area. The processor unit contacts the electrode 12 and reads out the voltage signals picked up by it. It includes an analog-to-digital converter so that the read out signal can be transmitted, by passive RFID communication, digitally to an external device.

Figure 5:
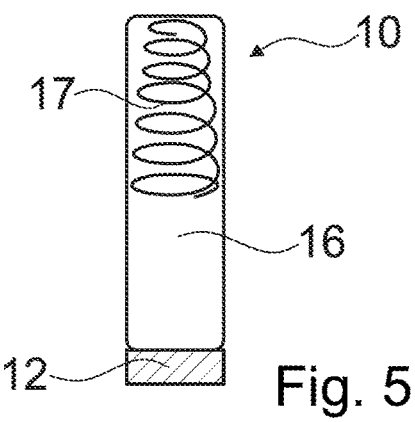
FIG. 5 yet another variant of an interaction pin with RFID chip and antenna.

The variant shown in FIG. 5 includes an integrated processor unit 16 with an antenna 17 all arranged within the interaction pin 10 that in this variant consists of an elongate, pin-shaped portion without a head portion.

Figure 6:
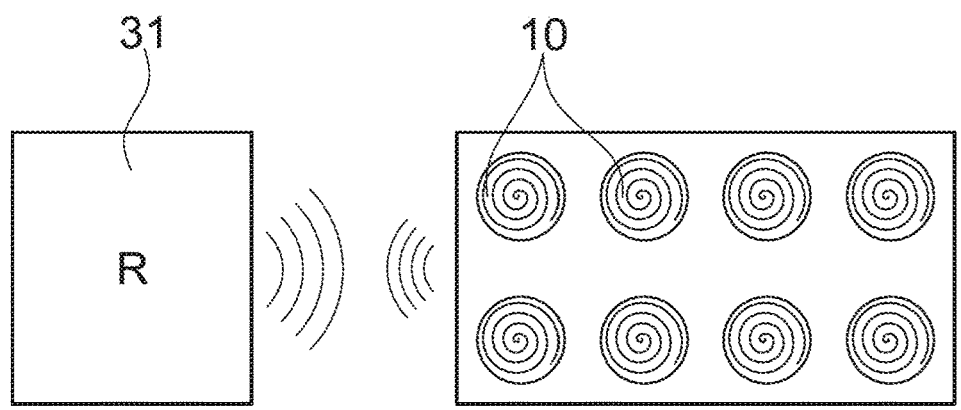
FIG. 6 a central reader unit communicating with an array of interaction pins.

FIG. 6 schematically depicts a central reader unit 31 capable of communicating with the interaction pins that each include an RFID antenna. The range of RFID communication with passive transponders (the interaction pins, unless they include a power source such as a battery, in these embodiments constitute passive RFID transponders) is, depending on the antenna and other factors, of the order of magnitude of a few meters, so the central reader unit 31 may, for example, be attached to the body, on the skull or somewhere else, for example the chest or the upper arm. Such a central reader unit may be implanted subcutaneously or, often preferred may be worn by the user on the body. Optionally, especially if the range is small, the apparatus may include a cap to be worn by the user, in which cap a plurality of read/write antennas is integrated.

Figure 7:
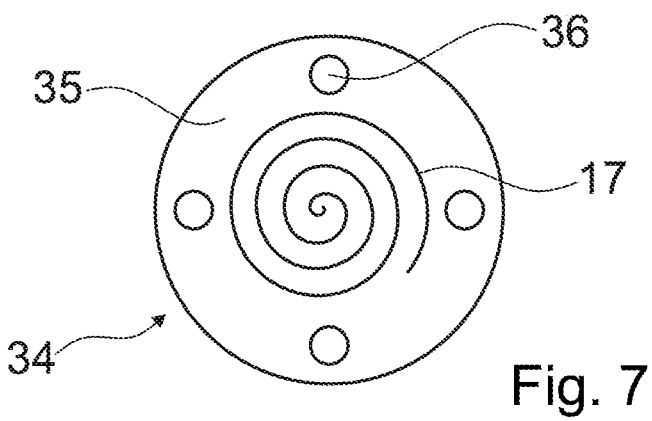
FIGS. 7-9 a possibility of fastening a transmitter unit.

FIG. 7 yet shows a transmitter unit 34, possibly with an amplifier. The transmitter unit 34 is configured to be placed on an outside of the cranial bone and to cooperate with interaction elements (of the kind described hereinbefore or of another kind) and to communicate with a further unit. The transmitter unit 34 includes a carrier 35, with an antenna 17 and possibly other electronic elements, such as a Digital-to-Analog converter and/or an amplifier. The carrier is fastened to the bone tissue by a plurality of fasteners 36.

The fasteners each include thermoplastic material for anchoring in the bone tissue. As illustrated in more detail in FIG. 8, the fasteners are rather short and are configured not to penetrate the entire thickness of the cranial bone. More in particular, the cranial bone has an outer cortical layer 1.1, a trabecular bone region 1.2, and an inner cortical layer 1.3, and the fasteners 36 are configured to not penetrate the inner cortical layer 1.3. Also, a distal end of the fasteners is optionally configured to lay against the inner cortical layer 1.3 and to thereby expand as a result of the anchoring process, as further illustrated in FIG. 9.

Figure 8:
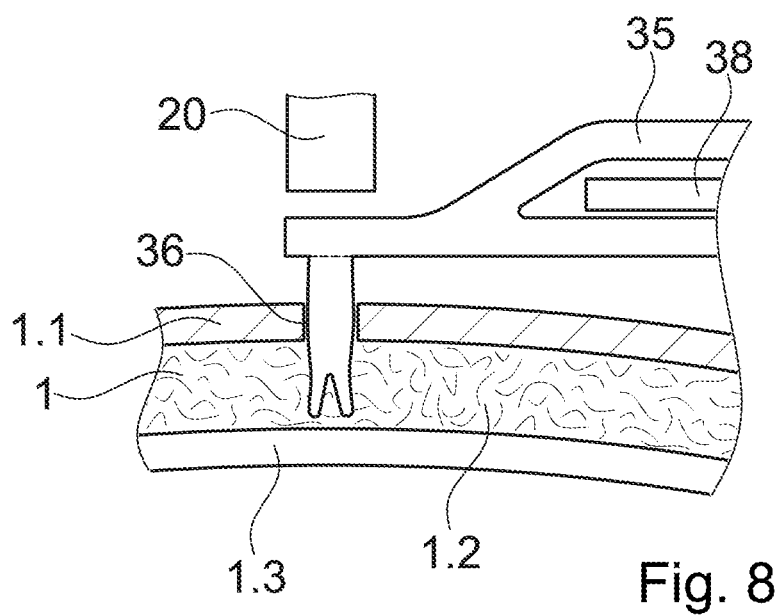

As sketched by the dashed line in FIG. 8, the fasteners 36 can be separate parts or integral with the carrier 35. FIG. 8 also shows an electronics unit 38 carried by the carrier and embedded by carrier material.

For fastening, the following processes may be used.

According to a first possibility, initially bores are made in the outer cortical layer 1.1—and possibly at least to some depth in the spongy bone 1.2—, and fasteners are then placed therein. Then, the carrier is placed relative to the fasteners, and the fasteners are one by one anchored by means of a sonotrode 20 that couples energy and a pressing force via the carrier into the respective fastener. The fastening of the carrier to the fasteners may be carried out at the same time, and potentially by the same process (resulting for example in a weld) or separately and/or by another process.

According to a second possibility, the fasteners are integral with the carrier. Also in this, firstly bores are made in the outer cortical layer 1.1. To this end, the carrier may come with a drilling template. Then the carrier with the fasteners is placed relative to the holes, and the fastening process is carried out like for the first possibility.

According to a third possibility, firstly holes are made in the outer cortical layer, and then the fasteners are placed and anchored, for example again by a sonotrode and mechanical vibration, as for example described in WO 02/069 817. Then, the carrier is fastened to the anchors, for example by welding or another method as described in WO 2008/128 367.

Figure 9:
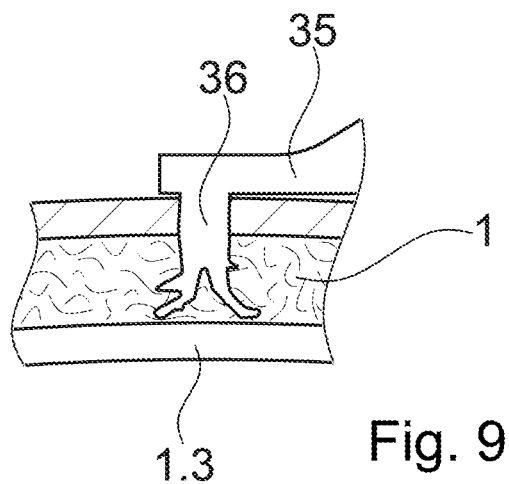

This principle as illustrated referring to FIGS. 7-9 makes two aspects possible. Firstly, it is possible to fasten, in a little invasive way, a flattish object that may include electronic components directly on the skull. Secondly, because only the outer cortical layer is opened, it makes a better protection of the brain and the meninges from injuries and infections possible.

As mentioned previously, in embodiments like the ones shown in FIGS. 1-9, in addition or as an alternative to including EEG electrodes or cooperating with EEG electrode, the interaction pins may also include at least one of:

A micro drug or nutrient or marker delivery system;
An actuator e.g. electro-magnetic or piezo-electric or pneumatic stimulator;
Sender (transmitter) coils for high-resolution MM for long-term intensive care of a patient with complex brain trauma;
A sensor, for example to measure the intracranial pressure or brain temperature;
An ultrasonic sonotrode;
A piezo speaker;
An optical sensor, such as a camera, for optical analysis like near-infrared;
A light conducting or light emitting element, for example a laser diode.

Especially, the combination of an electrode with at least one of a drug delivery mechanism or an actuator, such as a deep brain stimulator, an electro-magnetic or piezo-electric or pneumatic stimulator, may be advantageous for therapy, for example in anticipating and preventing an epileptic seizure.

Figure 10A:
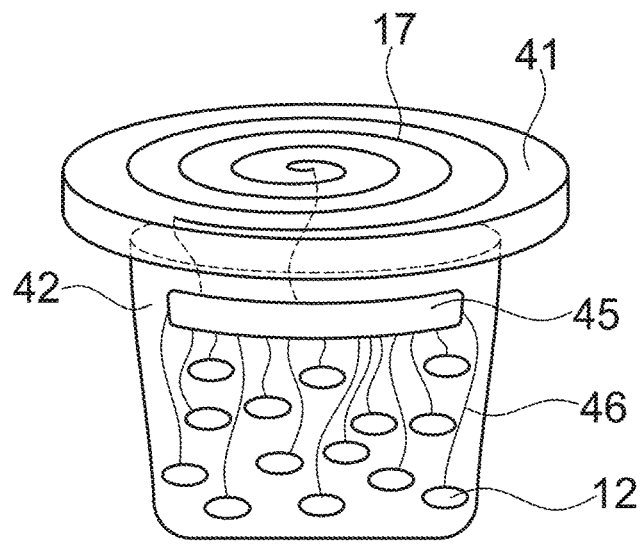
FIG. 10a 10d, in a side view and a top view, device with an electrode carrier and a fastening portion, and variants of outer edges of such device.
Figure 10B:
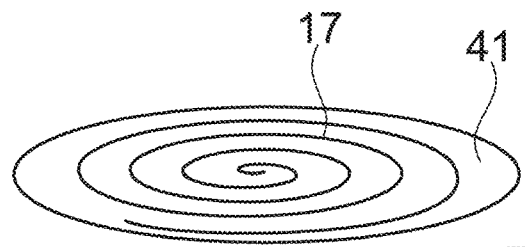

An example of an electrode carrier device according to the second aspect of the invention is depicted in FIGS. 10a and 10b. The device includes a fastening portion 41 and an electrode carrier 42. The electrode carrier is provided as a flexible, bendable circuit board of a biocompatible material and carries an array of electrodes 12 that are connected with a processing unit 45 by conductor paths 46. Also, the conductor paths (if exposed) and the electrodes 12 are of a biocompatible material, for example of Gold or possibly Titanium or Carbon. The processing unit 45 is connected to the antenna, by which it is powered and read by a reader unit.

Figure 10C:
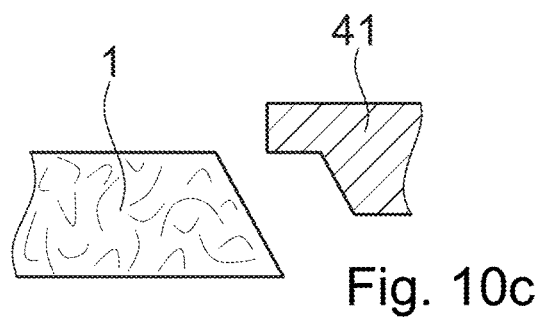
Figure 10D:
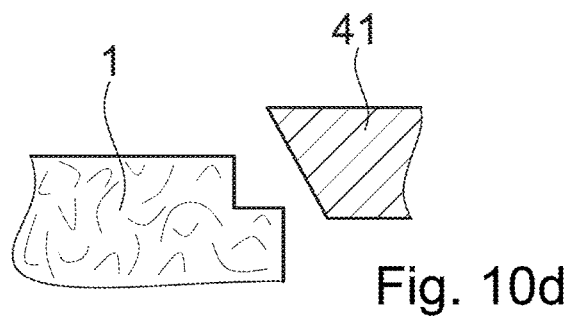

FIGS. 10c and 10d show different variants of circumferential edges of a fastening portion 41 together with bone tissue 1. The combination of a step feature of the fastening portion or the bone with a taper of the bone or the fastening portion, respectively, or the combination of step features or tapers of both or any other cross section that confines the forward path of the device with respect to the bone tissue brings about both, a tight seal along a full periphery of the fastening portion as well as very short fastening path (path made by the fastening portion into a distal direction while energy impinges) of only between 0.2 mm and 2 mm. This protects the soft tissue from damages. In addition, the exposition to energy (especially mechanical vibration energy) in terms of time and path is kept small, and the exposition to heat is very local around the periphery of the fastening portion and far away from the Dura.

Figure 11:
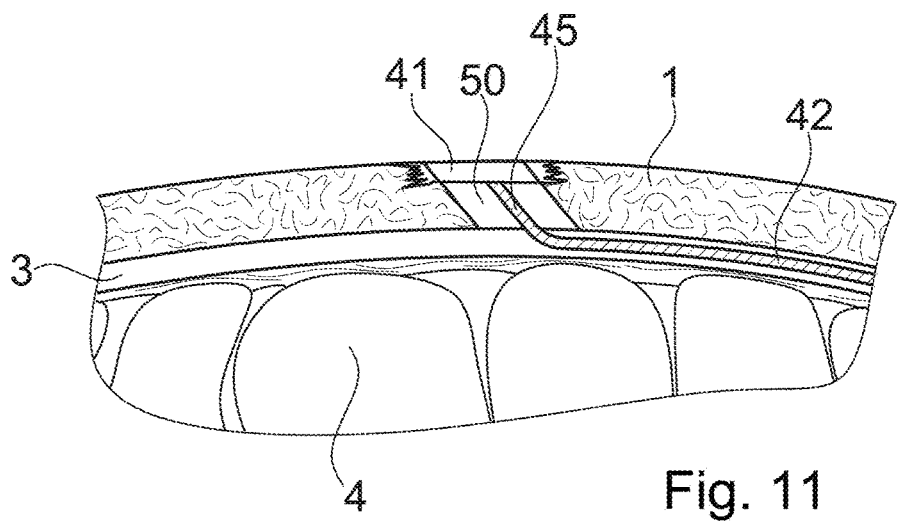
FIG. 11 the device of FIGS. 10a and 10b in an implanted state.

FIG. 11 depicts a device of the kind shown in FIGS. 10a and 10b in an implanted state (the scalp not being shown in FIG. 11). The cranial bone 1 is provided with a slit-like through opening 50 through which the electrode carrier 42 is inserted. The fastening portion 41 is anchored in the bone tissue of the cranial bone by being subject to energy, especially mechanical vibration energy while and/or before it is pressed against the tissue, so that the thermoplastic material is liquefied and after re-solidification forms an anchoring as well as a tight seal.

In addition to be attached to the fastening portion 41, the electrode carrier 42 may further be secured to the tissue, for example by being attached to the inner side of the skull or to a separate element as explained in further detail hereinafter. Alternatively, the electrode carrier may be held in place merely by the fastening portion 41 and the fact that the space between the meninges 3 and the cranial bone 1. As an alternative to being arranged between the meninges and the cranial bone, the electrode carrier could also be possibly anchored subdurally or even closer to the brain.

Figure 12:
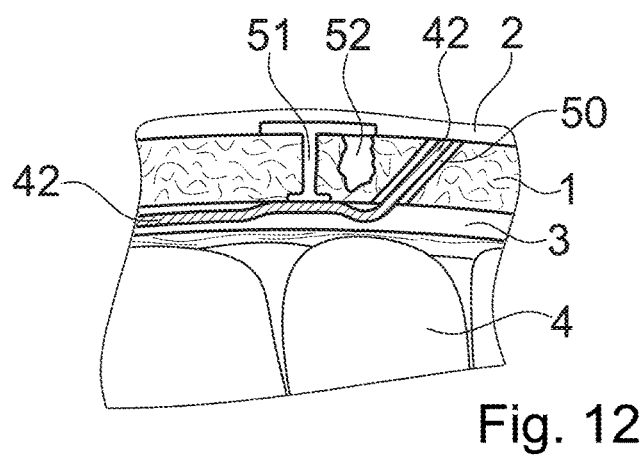
FIG. 12 a device including an electrode carrier and a fastening element, in an implanted state.

In accordance with the variant shown in FIG. 12, the device includes a fastening element 51 reaching through the cranial bone 1. A distal end of the fastening element 51 includes a mechanical coupler, for example constituted by a magnet, or a an engaging mechanism. The electrode carrier 42 is again inserted through the slit-like opening 50. It is further secured to the fastening element by including a mating mechanism (magnet/magnetizable material; engaging structure etc.) corresponding to the mechanical coupler of the fastening element 51. The fastening element itself may be formed as an element including a thermoplastic material at least on an outer side thereof so that it is capable of being anchored similarly to the interaction pins described hereinbefore. As a further alternative, the fastening element 51—like in the illustrated embodiment—may be of a not liquefiable material but be anchored by an anchor 52 (anchoring pin) that includes thermoplastic material and is anchored by the process substantially as described in WO 02/069 817. Alternatively, a fixation like the one that is subject to EP 2 063 793 B1 may be envisaged. Especially, a wedge-shaped anchoring element including thermoplastic material may be pushed into the slit-like opening while energy acts on it until it is liquefied at least in part and anchored in the bone tissue, leading both, to anchoring and to a sterile seal.

The electrode carrier may further be secured to the tissue—and thereby the interior sealed from the outside—in a manner as illustrated in FIG. 11, or alternatively, sealing may be implemented by conventional means. The electrode carrier may include a processing unit as illustrated in FIG. 10a, or the conductor paths from the electrodes may provide a galvanic connection between the electrodes and an outside so that the electrodes are contactable by a plug-and-socket connection for example.

In addition or as an alternative to being mechanically coupled to a fastening element, the electrode carrier may include an anchor that includes thermoplastic material or a thermoplastic portion and be fastened to the inner side of the cranial bone in a manner described hereinafter for the third aspect of the invention.

Figure 13:
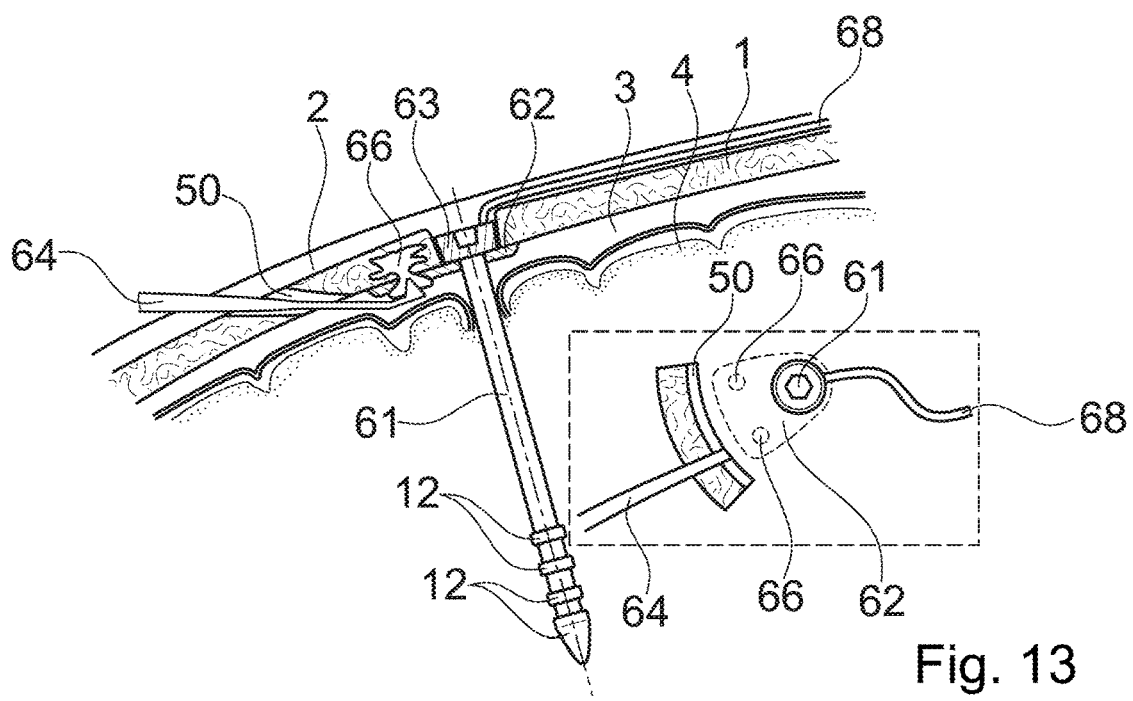
FIG. 13 a section through a part of a human skull with a DBS as a first example of electrode fixation for deep brain stimulation.

FIG. 13 depicts a first example of electrode fixation for deep brain stimulation. FIG. 13 shows a part of the skull with the inserted DBS electrode carrier 61 during fixation; the insert (dashed box) depicts a top view on the skull without the scalp. The DBS electrode carrier is an elongate needle-like pin with a head 63 extending straight along an axis. It carries, in a region towards the distal end, at least one electrode 12, namely four electrodes in the depicted embodiment. The DBS electrode carrier is of an electrically insulating material, or the electrodes are electrically insulated from the DBS electrode carrier. The electrodes are electrically contacted from the proximal side by conductors running through an interior of the DBS electrode carrier 61.

The DBS electrode carrier includes a pin head that partially is sunk in the cranial bone tissue and from which an electrical cabling 68 contacting the electrodes leads to an external processing unit, for example subcutaneously. As an alternative to electrical cabling, the device may also be equipped for wireless connection, especially if the DBS electrodes are primarily used for measurement purposes and not primarily for stimulation. For wireless connection, especially wireless readout, the device may for example include an integrated processor unit and an antenna, like in the hereinbefore described embodiments.

The device further includes an anchoring body 62 cooperating with the DBS electrode carrier 61 to anchor the latter in the tissue. In the embodiment of FIG. 13, the anchoring body 62 runs immediately underneath the cranial bone and is attached thereto. For attaching the anchoring body, the device includes a plurality of anchors 66 each including thermoplastic material.

The device is implanted as follows:

In a first step, a hole is drilled into the skull as known for insertion of DBS electrodes. Also, before or after this, a slit-like through opening 50 is made in the skull, in a vicinity of the drilled hole. This may for example be done by ultrasonic cutting.

Then, the anchoring body 62 is inserted through the slit-like opening 50 so that a guiding opening of the anchoring body 62 is approximately aligned to the hole. In a variant, the anchoring body may be placed prior to the drilling of the hole, for example if an imaging method allows to exactly locate the anchoring body, whereby the anchoring body may also serve as guide during the drilling step.

Thereafter, the DBS electrode carrier 61 is inserted through the hole. During the insertion, the position of the anchoring body 62 can be adjusted for example by adjusting the orientation of the DBS electrode carrier 61. As known from DBS electrode implantation, feedback for the placement of a DBS electrode may be obtained from the patient himself or by an imaging method, such as MRI.

Figure 14:
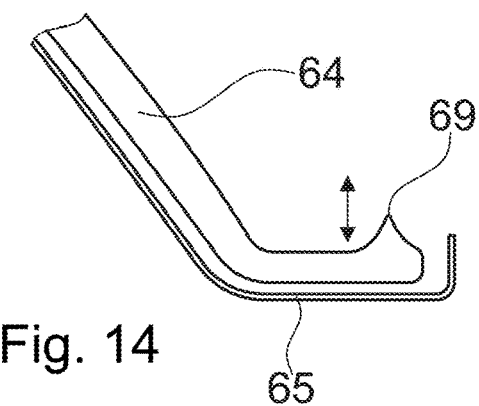
FIG. 14 a tool for anchoring body or electrode carrier fixation from inside the skull.

After the DBS electrode has reached its final position (FIG. 13), the anchoring body 62 is fastened to the cranial bone. To this end, the at least one anchor 66—the two anchors in the depicted configuration—is/are anchored in the bone tissue to fasten the anchoring body. For anchoring one of the anchors 66 is placed relative to the tissue, and a tool 64 is used to couple a proximally directed pressing force and mechanical vibration energy into the anchor, whereby the thermoplastic material is liquefied at least locally and pressed into structures of the bone tissue to form, after re-solidification, a positive-fit connection with the bone. The tool (sonotrode) 64 is to this end inserted through the slit-like through opening. It includes a proximally-facing outcoupling protrusion that allows applying the force and the vibrations in a targeted manner. As further illustrated in FIG. 14, it may further include a protecting screen 65—for example in the form of a sleeve with an opening for the outcoupling protrusion 69—that protects tissue distally of the tool 64 from the vibrations.

Instead of the device including separate pin-like anchors (with heads for securing the anchoring body 62 against the tissue), the anchoring body itself may include regions of thermoplastic material, and the outcoupling protrusion may be used to tag the anchoring body 62 locally to the bone tissue.

A set-up similar to the one depicted in FIGS. 13/14 may optionally be used to secure an electrode carrier of the kind described referring to FIGS. 10a-12 against the bone tissue.

Figure 15:
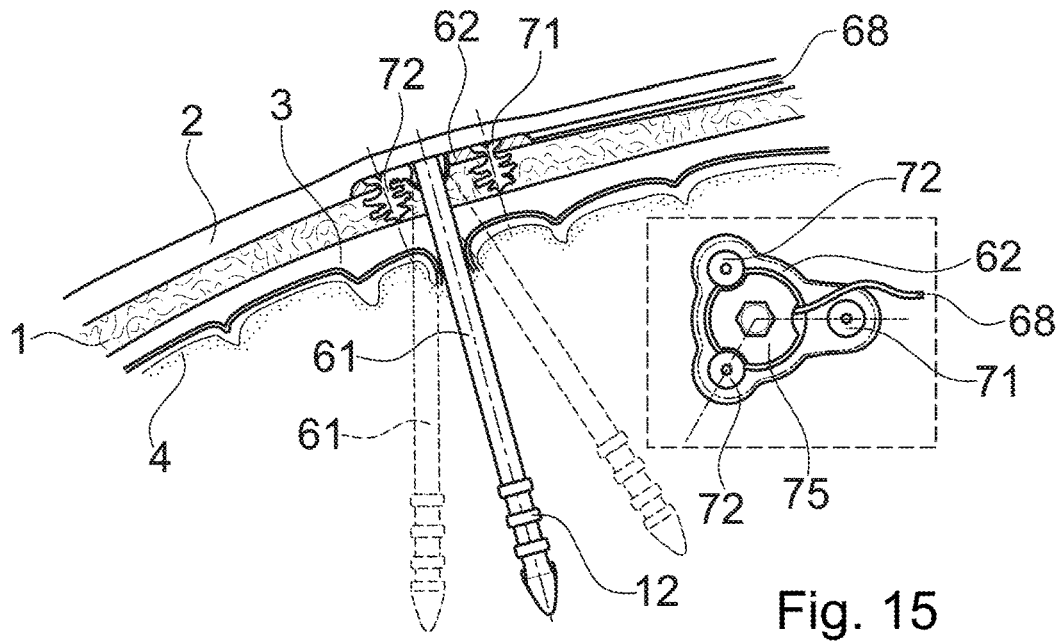
FIG. 15 a second example of electrode fixation for deep brain stimulation.

In the embodiment of FIG. 15, in contrast to the embodiment of FIG. 13, the anchoring body 62 is configured to be fastened to an outside of the cranial bone tissue. As a consequence, the slit-like opening is not necessary.

For implantation, a hole for the DBS electrode carrier 61 is made, and the anchoring body 62 is placed on the outer surface of the cranial bone 1, with the through opening of the anchoring body 62 aligned relative to the hole. A fastening anchor 71 may be used to fasten the anchor carrier to the tissue. The fastening anchor 71 in this may include thermoplastic material and may be fastened by vibration energy as described for anchors hereinbefore. This kind of anchoring has the advantages of being particularly quick and economical, and of having the possibility of using resorbable materials. Alternatively, other kinds of anchors, such as a bone screw or similar may be used.

The DBS electrode carrier 61 is inserted through the anchor carrier. A ball joint like surface leaves the possibility of inserting the electrode carrier 61 in various different angles, as schematically illustrated by the variants shown in dashed lines. Also in this embodiment, during the insertion, the position of the DBS electrode carrier 61 is adjusted, and feedback for the placement of the electrode carrier is obtained by an imaging method and/or by reactions of the patient.

After the DBS electrode carrier has been inserted, its orientation relative to the anchor carrier is fixed by two fixation anchors 72. The fixation anchors 72 in addition to further fastening the anchoring body 62 to the bone tissue also block any remaining rotational degree of freedom of the DBS electrode carrier 61 relative to the anchor carrier 61.

A cover 75 may be applied to the anchor carrier after the fixation for ensuring that the surface of the device that later is covered by the scalp is smooth.

Also FIG. 15 depicts the device with electrical cabling 68 for contacting the electrodes. Also the embodiment of FIG. 15—as well as the embodiment of FIG. 16 described hereinbelow—may as an alternative to electrical cabling also be equipped for wireless connection, especially if the DBS electrodes are primarily used for measurement purposes and not primarily for stimulation.

Figure 16:
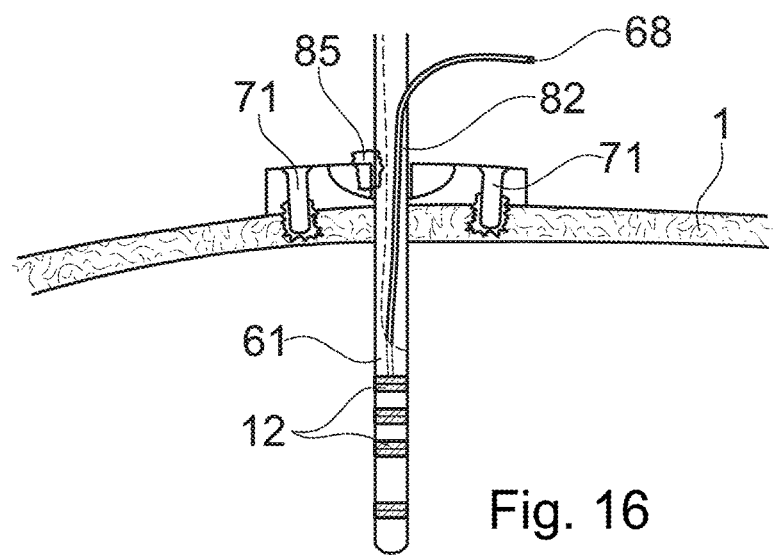
FIG. 16 a third example of electrode fixation for deep brain stimulation.

FIG. 16 yet shows an embodiment that is based on a similar principle as the embodiment of FIG. 15, but with the possibility to adjust the depth of the DBS electrodes 15. To this end, a DBS electrode carrier of adjustable length is used. More in particular, the DBS electrode carrier 61 is provided with an excess length. After placement and anchoring of the anchoring body 62 (by means of anchors 71, for example of the kind mentioned hereinbefore), the DBS electrode carrier is introduced until it reaches the appropriate depth. The DBS electrode carrier is provided with a slit opening 82 through which the electrical cabling 68 is guided out of the interior. As soon as the appropriate depth has been reached, a fixation anchor 85 may be used for fixing the DBS electrode carrier relative to the anchoring body. The excess length of the DBS electrode carrier 61 is then cut off, and the slit opening 82 through which the electrical cabling is guided out of the interior of the DBS electrode carrier is sealed.

For the fixation anchor 85 as well as possibly for the fixation anchors 72 of FIG. 15, the anchoring body 62 may locally have a structure into which liquefied thermoplastic material of the fixation anchor may penetrate, for example an open porous structure. Appropriate such structures have been described in WO 2008/034 276. Interpenetration of such structures by liquefied thermoplastic material leads, after re-solidification, to a positive-fit connection. As an alternative to such a positive-fit connection or in addition thereto, also other kind of connections, for example a glue connection may be used.

Figure 17:
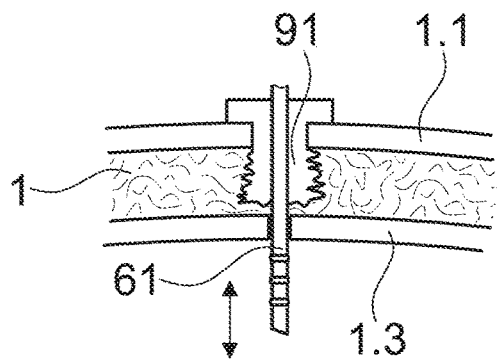
FIGS. 17 and 18 a forth example for electrode fixation for deep brain stimulation, by an anchoring body that is constituted by a single anchor.

FIG. 17 depicts a further embodiment, in which anchoring body consists of thermoplastic anchor. The thermoplastic anchor 91 in this is anchored unicortically, similarly to the anchors described referring to FIGS. 7-9. However, the anchor 91 includes a central axial opening through which the electrode carrier 61 runs and by which it is guided. The electrode carrier 61 further is guided through an opening in the inner cortical layer 1.3 and may be displaced relative to the anchor 91 in axial directions until the electrodes have reached a desired position. Then, the relative position is fixed by an appropriate means, for example an adhesive applied to the proximal side, or by a separate clamping mechanism or similar. As yet another alternative, the fixation may be caused by a separate thermoplastic fixation element pushed between the electrode carrier and the anchor while energy impinges thereon, especially if the electrode carrier has surface structures that allow interpenetration by liquefied thermoplastic material to yield, after re-solidification, a positive fit connection. At the same time, the thermoplastic material will be welded to the anchor 91, thus fixing the anchor and the electrode carrier relative to one another.

Figure 18:
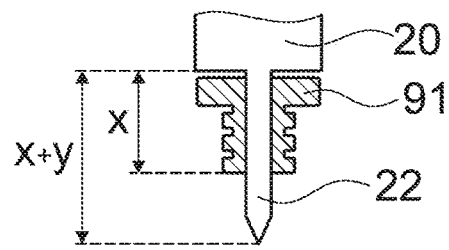

The process by which the thermoplastic anchor is anchored may be combined with a process of making the opening in the inner cortical layer for the electrode carrier 61. FIG. 18 illustrates a tool that is a sonotrode with a guiding and piercing needle 22 on which the anchor 91 sits. The difference y between an axial extension x of the anchor 91 and an axial extension of the needle 22 may be chosen according to the needs. If x is approximately equal to a thickness of the cranial bone, then y should be small (for example not more than 1 mm), and bicortical anchoring will result. If x is smaller, y can accordingly be longer (for example between 2-5 mm), and unicortical anchoring (like in FIG. 17) will result, with the needle making the hole for the electrode carrier.

Figure 19:
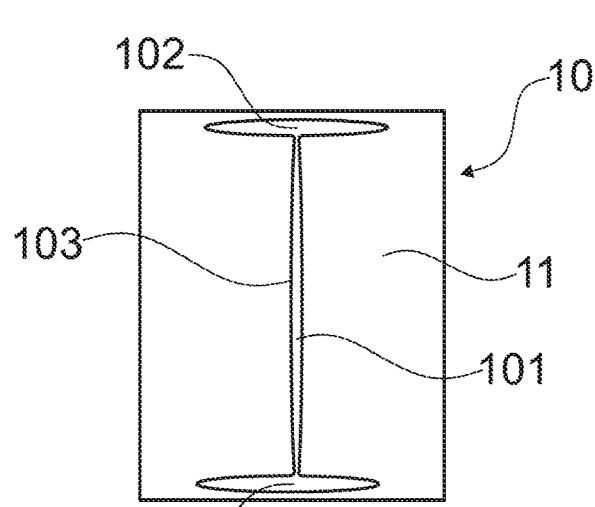
FIGS. 19 and 20 interaction pins suitable of being buried under tissue, especially the skin.

FIG. 19 shows an example of an interaction pin 10 with an interaction element 101 in the form of an electrically conducting bridge between a proximal interaction point and a distal interaction point. In the depicted embodiment, the proximal and distal interaction point each have an interaction electrode 102, 104, the electrodes being conductively connected by a connecting conductor 103. A potential variation inside caused by brain activity will influence the electrical potential of the distal electrode and thereby also of the proximal electrode. In practice, this implies that small electrical charges flow between the proximal and the distal electrodes to compensate possible potential differences between the inside and the outside caused by the electrical fields inside, thus effectively transferring the electrical field (or to be precise: its component along proximodistal directions) distally of the conducting bridge to proximally of the conducting bridge. A readout device close to the proximal electrode may be used to sense the electrical potential of the conducting bridge. Such readout device may for example be placed atop skin tissue that covers the proximal end face of the interaction pin.

Of course, the same considerations apply the other way round: if a signal is to be delivered to the central nervous system, a signal supplying device may be placed close to the proximal electrode, and the potential variations applied by this signal supplying device may be transferred to the interior of the skull by the conducting bridge. More in general, the proximal electrode will interact with an interaction device that will in most cases be capable of interacting with each interaction element individually, i.e. that has a resolution at least corresponding to the distance between neighboring interaction elements.

The conducting bridge may reach to the distal end and/or the proximal and form a part of the respective end face. Alternatively, the conducting bridge may be embedded in non-conducting material, as shown for example for the proximal electrode 102 in FIG. 19.

Figure 20:
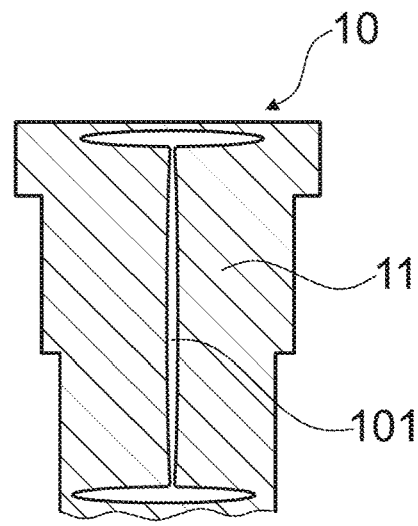

FIG. 20 shows a variant in which the thermoplastic portion 11 is provided with outer steps and/or other energy directing and/or material flow directing features. More in general, embodiments with a conducting bridge ("buried electrode") may be realized with any suitable shape of the interaction pin, that makes it suitable for being anchored in the tissue by the joint effect of energy, especially mechanical vibration energy, and a pressing force, whereby portions of the thermoplastic material are made flowable and pressed into structures of the tissue to yield an anchoring. This includes but is not limited to structures that are disclosed referring to other embodiments described in this text, as well as structures known from the references cited herein.

Figure 21:
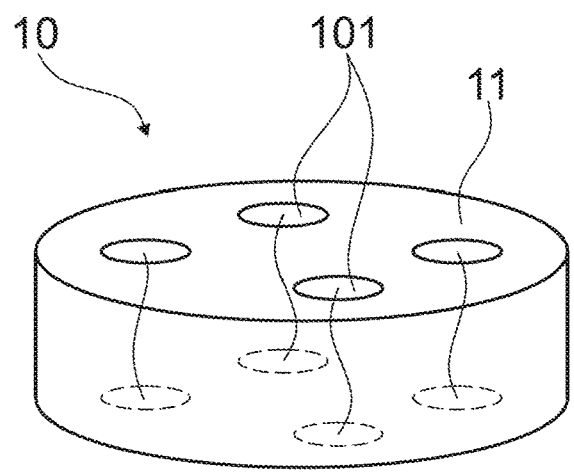
FIG. 21 an interaction pin suitable of being buried under tissue, the interaction pin including a plurality of interaction elements.

FIG. 21 shows an embodiment in which one interaction pin 10 has a plurality of interaction elements 101, each for example of the kind described referring to FIGS. 19 and 20. Embodiments with a plurality of interaction elements per pin may be advantageous in special circumstances, for example if the number of operation sites on a patient need to be limited, etc.

Figure 22:
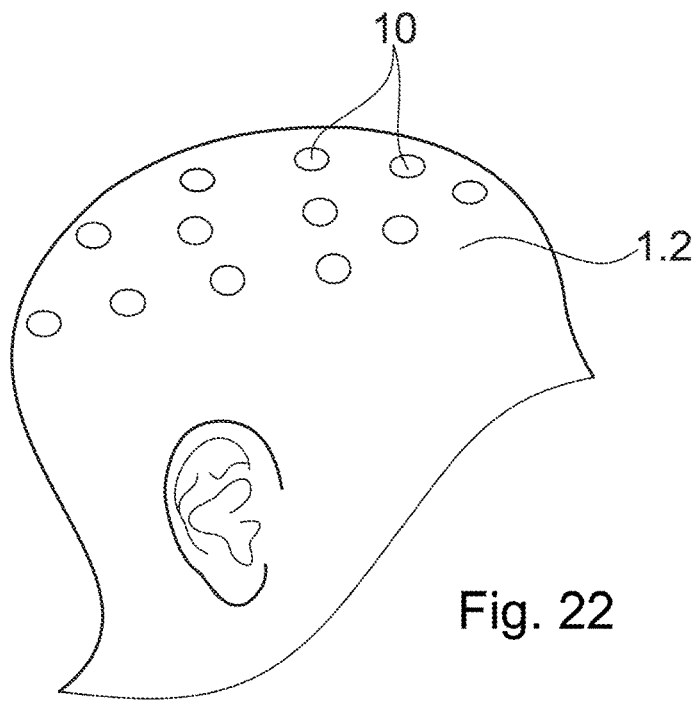
FIG. 22, the locations of an array of buried interaction pins implanted in a head.

FIG. 22 depicts an arrangement of individual interaction pins 10, each for example of the kind of FIGS. 19 and 20, on a human skull. In reality, the interaction pins would not be visible from an outside because they are covered by the scalp.

Figure 23:
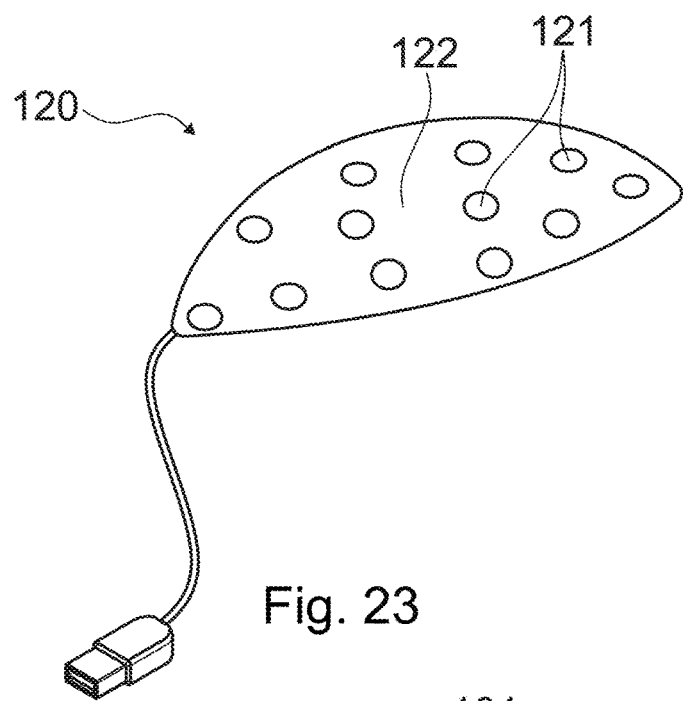
FIG. 23 an interaction device for the array of FIG. 22.

For patients suffering from certain conditions making frequent interaction with the central nervous system necessary, the arrangement of interaction pins may be implanted once and remain there for long time spans, for example for years, without any post-treatment or maintenance necessary, as the bridges formed by the interaction pins are purely passive. At least the interaction elements are of an inert material. The thermoplastic material may also be chosen to be inert (not resorbable). In special embodiments, the interaction elements may be provided with a material and/or structure suitable for osseointegration, and the thermoplastic material may be resorbable, so that after some time the thermoplastic material has disappeared and the interaction element is anchored in the head by osseointegration. In such cases, a special arrangement of the thermoplastic material, for example as taught in WO 2004/017 857, may be beneficial. FIG. 23 depicts an interaction device 120 in the form of a cap 122 fitting to the array of interaction elements of FIG. 22. The interaction device includes an array of device interaction points, here in the form of contacting electrodes 121 located at positions corresponding to positions of the interaction elements. The device interaction points are arranged on a carrier, for example a flexible carrier. The interaction device includes an interface for data communication and/or power supply. The contacting electrodes may for example be conventional electrodes as known form EEG. Alternatively, they could be such as to be capable of wireless signal transmission, as described referring to the fourth aspect.

The interaction device in the depicted embodiment includes a device control with signal processing means, and the interface to external devices is generic.

Figure 24:
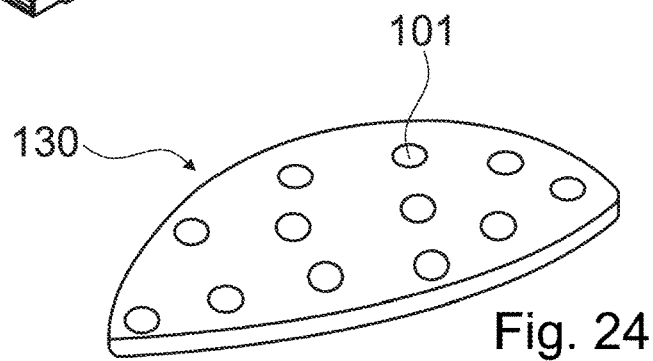
FIG. 24 an interaction implant including a plurality of interaction elements, the interaction implant being suitable as single implant.

FIG. 24 illustrates an interaction implant 130 that is similar to an interaction pin of the hereinbefore described kind, for example shown in FIG. 21, with a plurality of interaction elements 101. However, in contrast to the interaction pins, it has a larger area and thereby is suitable to serve as single implant that constitutes a permanent window (of an electrical, optical, or other kind) to the central nervous system, possibly also without belonging to an array of similar implants. The shape of the interaction implant 130 may be adapted to the shape of the bone tissue in which it is implanted and/or which it replaces.

Figure 25:
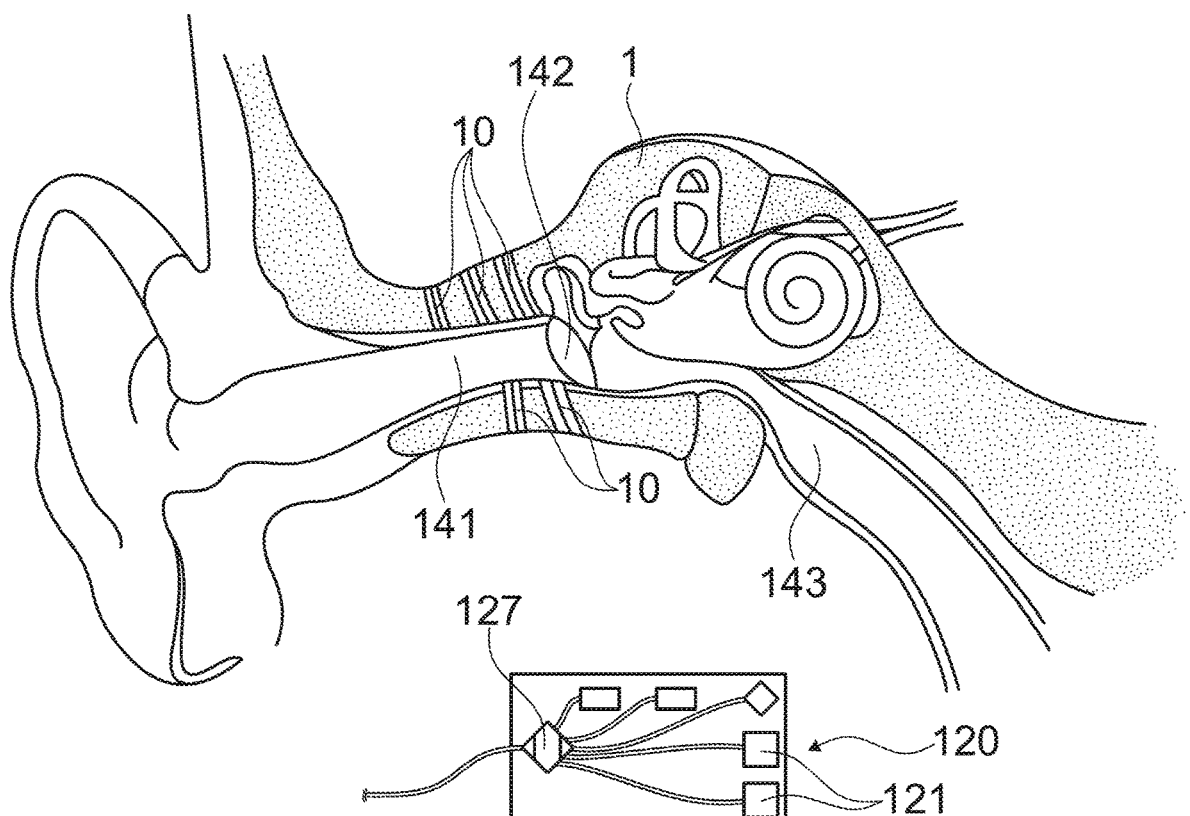
FIG. 25 an arrangement of interaction pins implanted in the cranial bone from the ear canal; and an according interaction device.

In an embodiment, the sensing and/or delivery headpiece may include one or more interaction pins implanted from the ear canal. This location features the special advantage that interaction with central brain regions becomes possible without any necessity of invading them. FIG. 25, illustrating a human ear with an ear canal 141, the tympanic membrane 142, the middle ear, and the Eustachian tube 143, shows such an embodiment. The interaction pins 10, for example of the kind illustrated in FIGS. 19 and 20, penetrate the bone tissue surrounding the ear canal into different directions, for example a three dimensional arrangement round the ear canal is possible.

An interaction device 120 as shown in the lower panel of FIG. 24 may have the shape of an ear mould or be configured as flexible (for example of silicone or similar) element. More in general, the interaction device 120 may have a carrier of a kind known from ear pieces of hearing instruments. Again, the arrangement of the interaction points 121 (here: electrodes) may be adapted to the arrangement of the interaction elements. FIG. 24 also depicts a processor unit 127 for controlling the interaction elements.

For designing the interaction device—this also pertains to embodiments where the interaction pins are at locations different from the ear canal and/or for combined application—for example, firstly the interaction pins may be set and then their position measured and the interaction device may be tailor-made to fit the position of the interaction pins. Additionally or as an alternative, a template may be used for the setting of the interaction pins. Additionally or as yet another alternative, the interaction device may have flexible positions of the interaction points, or may have an area-wide interaction field with sufficient resolution to distinguish between the locations of the interaction elements.

Figure 26:
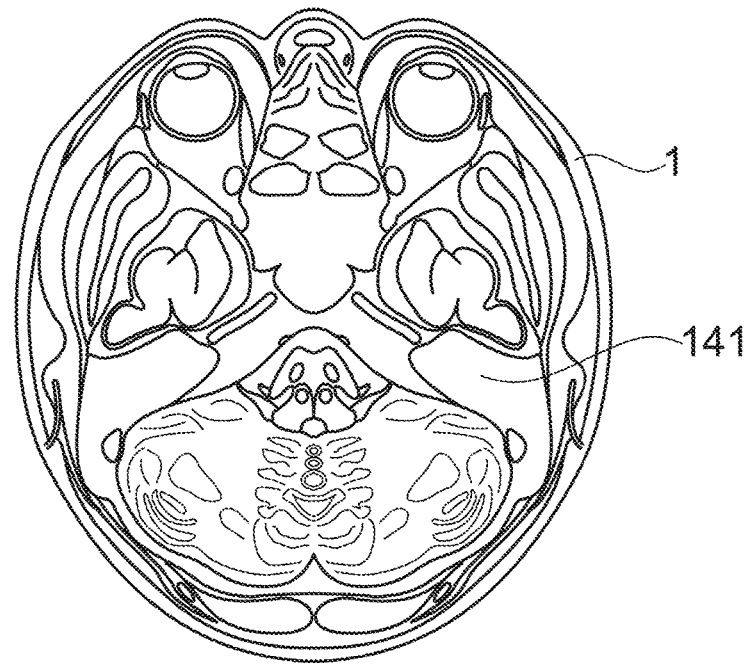
FIG. 26 a transversal section of a skull illustrating the position of the ear canal.
Figure 27:
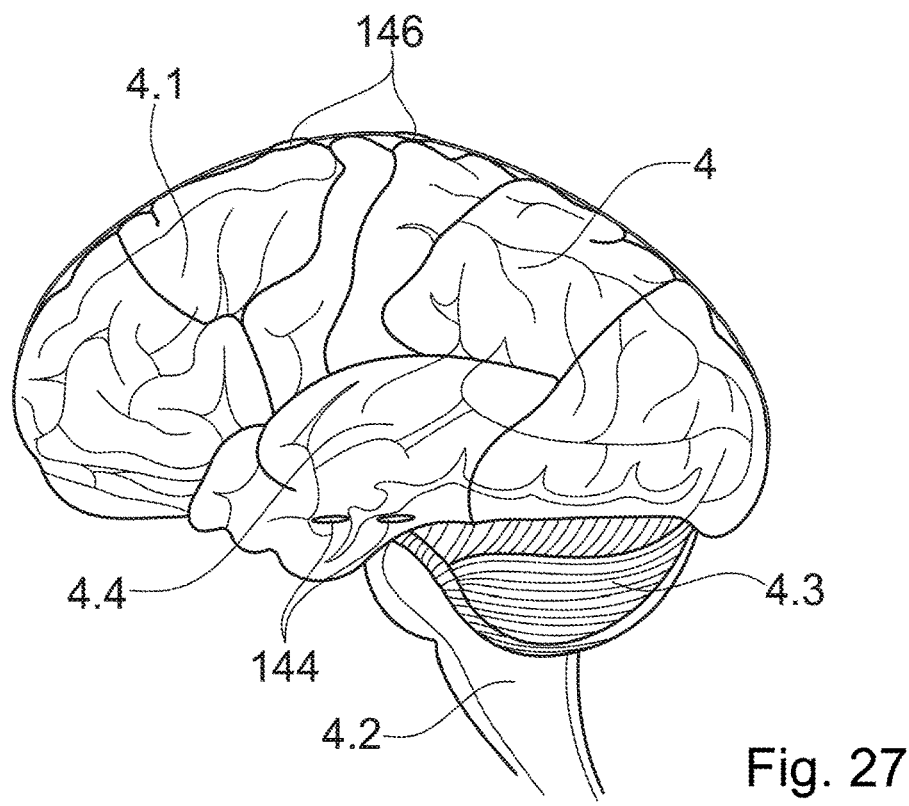
FIG. 27, schematically, a sagittal cross section of the brain illustrating possible positions of electrodes implanted from the ear canal and of reference electrodes.

The advantages of implanting an interaction element (electrode, light conductor, optically active element, etc.) from the ear canal—this pertains to all aspects of the present invention, including the second aspect (wherein interaction elements are constituted by the electrodes), the third aspect and the fourth aspect—become especially clear from FIGS. 26 and 27. FIG. 27 schematically shows the brain with the telencephalon 4.1, the brain stem 4.2, the cerebellum 4.3 and, shown schematically, the location of the limbic system 4.4. The ear canal 141 makes positions close to all of the brain stem 4.2, the cerebellum 4.3 and the limbic system 4.4 accessible that otherwise would be very difficult to reach by electrodes or other interaction elements that are not to go through the brain.

FIG. 26 in addition to possible positions 144 of electrodes as examples of the interaction elements schematically shows positions 146 of reference electrodes, that also may be formed and implanted according to an aspect of the invention. Alternatively to the positions atop the skull, other positions are possible, depending on which region of the brain is to be accessed, including posterior positions, posterior-caudal positions (for accessing the cerebellum and the brain stem), anterior positions (for example for the visual center), or lateral positions, including the possibility of obtaining a right-left resolution of the signals.

Figure 28A:
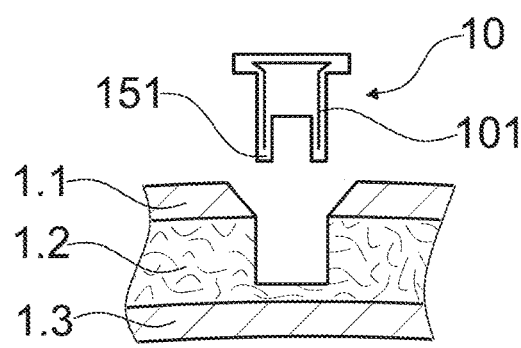
FIGS. 28a and 28b embodiments of an interaction pin.
Figure 28B:
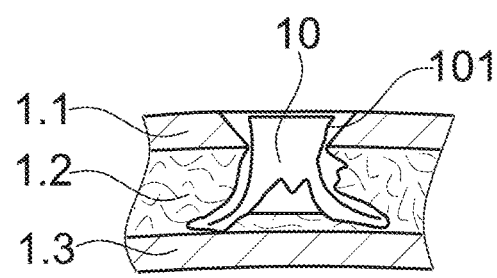

FIGS. 28a and 28b illustrate the possibility of providing the implant carrying an interaction element, especially an interaction pin according to the first aspect of the invention, in a configuration in which the cranial bone is not completely broken through but in which the implant (interaction pin 10) is implanted in a blind hole in the tissue. The interior cortical bone tissue 1.3 is left intact. The interaction pin 10 has distal feet 151 that support a deformation of the distal end portion as soon as the distal end of the interaction pin gets into contact with the more dense cortical bone under the effect of the impinging pressing force and energy (especially mechanical vibration energy). The resulting deformation is shown in FIG. 28b.

The shown interaction pin 10 is illustrated to have an interaction element 101 in the form of an electrically conducting bridge, and the deformation brings about an increased interaction surface on the interior, distal side. However, the configuration schematically shown in FIGS. 28a and 28b also works for other kinds of interaction pins, including at least partially transparent optical interaction pins or interaction pins of an electrically conducting thermoplastic material in which the thermoplastic material itself is the interaction element.

Figure 29A:
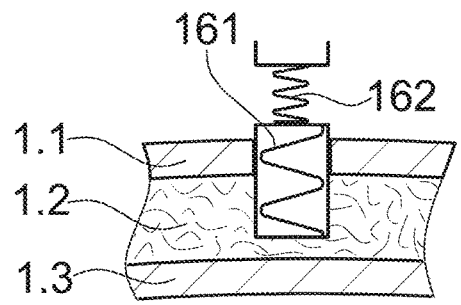
FIGS. 29a and 29b the drilling of a blind hole in the cranial bone for an interaction pin as shown in FIGS. 28a and 28b.
Figure 29B:
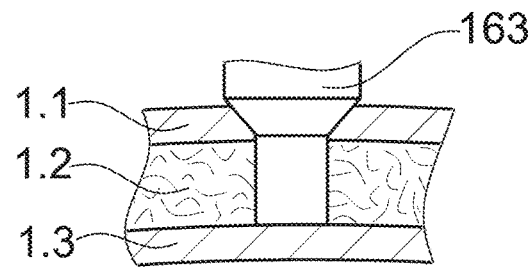

FIGS. 29a and 29b very schematically show how a blind opening as shown in FIG. 28 can be manufactured even if the thickness of the cranial bone is not known with sufficient precision. After the exterior cortical bone layer 1.1 has been locally removed, a drilling tool 161 with a flat distal end and with a force limiter 162 may be used. Because the resistance of the denser interior cortical bone layer 1.3 is much higher than the resistance of the spongy bone 1.2, the force limiter 162 will stop the drilling reliably. In an optional subsequent step (FIG. 29b), a beveling tool 163 can be used to bevel the blind hole.

FIG. 30 shows a close-up illustration of the distal end of an interaction pin (or other interaction implant) implanted in a blind hole with the interior cortical layer being intact. The thermoplastic material 11 interpenetrates the spongy bone and may reach into irregularities of the cortical bone 1.3 but will not reach the other side and especially leave the interior Periosteum 1.5 intact. In a configuration as the one of FIG. 30, the thermoplastic material 11 may be transparent (for coupling light into the brain through the very thin remaining bone layer) or may be electrically conducting for serving as an electrode.

FIG. 31 shows a variant of a distal end of an interaction pin of any one of the above discussed kinds, with the interaction pin having a plurality of feet. Optionally, the different feet may form or include different interaction elements, such as different electrodes. In this case, the electrodes may be electrically insulated from each other.

There are configurations, as shown referring to FIGS. 1a and 1b, in which it is desired that the distal end of the interaction element reaches through the cranial bone. FIG. 32 illustrates a further according example, wherein a distal end portion of the interaction pin 10 and an opening 171 of the interior cortical bone layer 1.3 are accordingly adapted to each other, the dimension of the opening 171 may be smaller than the dimension of the opening in the outer cortical bone layer 1.1 around which sealing and anchoring takes place.

FIG. 33 shows an embodiment of the variant of the configuration with a blind hole in which the interior-most lamella of the cranial bone is perforated by a very small perforation 181 only. Anchoring of the interaction pin 10 (or other interaction implant) may be carried out as described hereinbefore, for example referring to FIGS. 28a, 28b, and 30. However, some thermoplastic material will leak out of the perforation 181 and into the intracranial space. This portion will assume a droplet-like form because upon outward propagation it will, because there is no friction, rapidly cool. This droplet portion 182 may for example serve as electrode if the thermoplastic material is electrically conducting, or it may serve as "light bulb" (light distributing portion) if the device includes means for coupling light into the thermoplastic material and the thermoplastic material is sufficiently transparent.

In this and in other embodiments that include measures for irradiating the brain tissue via the thermoplastic material, a proximal end of the interaction pin (or other interaction implant) may be equipped to be coupled to a light guide or directly to a light source via an accessible contact face or via an access port described hereinafter. Alternatively, the interaction pin (or other interaction implant) may include the light source 191 itself, as schematically shown in FIG. 34. FIG. 34 shows the light source coupled to a coil element 17 that in this embodiment does not primarily serve as data communication antenna but is capable of receiving by electromagnetic induction power for the light source 191, here being illustrated as LED. The distal end portion 192 of material that has interpenetrated bone structures serves as diffusor for the light, as described in the mentioned WO 2005/105 208.

FIG. 35 yet illustrates an implant in the form of an access port. The implant has a basically disc shaped thermoplastic portion 11 that is anchored in a through opening in the cranial bone 1 by a method as described hereinbefore. The thermoplastic anchoring portion 11 carries, directly or indirectly via a carrier 152, an electrode 12 or other interaction element, for example a deep brain stimulation electrode carrier 61 or an electrical bridge 101 of the hereinbefore described kind. Proximally of the interaction element, a septum element 151 is arranged. The septum element 151 seals the portions distally of it from any region proximally of it. A contacting element 154, for example a needle, may be used to pierce the septum element 151 and to contact the interaction element for providing a reversible access to the permanently implanted interaction element.

In a variant of the concept shown in FIG. 35, the septum element 151 could be replaced by a removable according cap element that allows to reversibly have access to an interior of the intracranial space.

Figure 36:
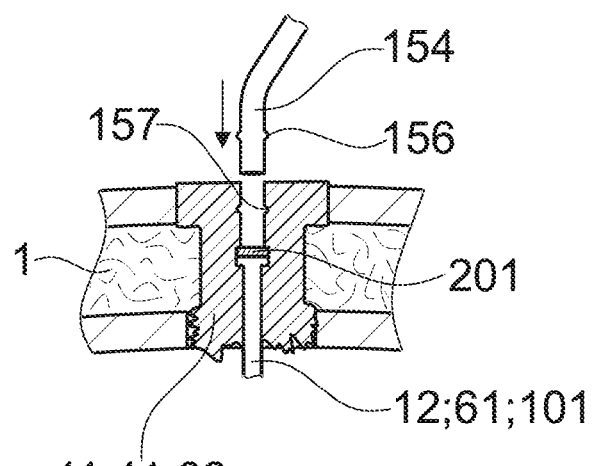
FIG. 36 another access port.

Also the embodiment of FIG. 36 is based on the concept of providing an access port for reversibly accessing a permanently implanted interaction element 12; 61; 101. In contrast to the embodiment of FIG. 35 and its variant with a cap element, the interaction element—for example electrode—remains permanently sealed from the contacting element 154. To this end, a membrane 201 that is a conductor for the signal to be transmitted but otherwise forms a tight seal separates the interaction element from the removable contacting element 154. If the interaction element is an electrode, thus the membrane is electrically conducting, and if the interaction element transmits light, the membrane is transparent for the light to be transmitted.

Implantation of a device as shown in FIG. 36 goes as follows: in a first step, the carrier 11, 41, 62 that includes the thermoplastic material is implanted by the method as described hereinbefore and used throughout this text, wherein energy and a pressing force impinge on the carrier to cause portions of the thermoplastic material to liquefy, interpenetrate structures of the bone tissue, and after re-solidification to form a positive-fit connection with the tissue. The carrier may initially have a central proximodistally running through opening as shown in FIG. 36. Then, the interaction element is inserted, and thereafter the membrane 201 is fastened to the carrier in a sealing manner, for example by welding. The access port can be accessed reversibly by a contacting element 154. To this end, the scalp may have to be pierced if it has healed above the device.

FIG. 36 also shows a retention structure 156 cooperating with a mating retention structure 157 of the carrier, whereby the reversible connection is a snap-in connection.

Figure 37:
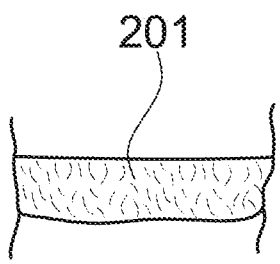
FIGS. 37 and 38 examples of membranes for the access port of FIG. 36.
Figure 38:
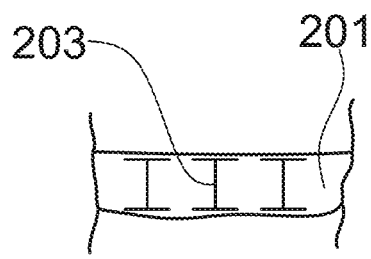

The membrane 201, in case it is electrically conducting, may be a of a thermoplastic material doped by a metallic filler, as illustrated in FIG. 37, or include conducting bridges 203, as illustrated in FIG. 38 or even be fully metallic.

Accordingly, the invention, according to a further, fifth aspect, concerns an access port, especially of the kind described referring to FIGS. 35-38, that includes a fastening portion (carrier), which fastening portion includes a thermoplastic material and is equipped for being anchored in bone tissue of the cranial bone by being subject to energy, and being pressed against the tissue, so that the thermoplastic material is liquefied and after re-solidification forms an anchoring as well as a seal. In this, the fastening portion includes a through opening. On a distal side with respect to the through opening, an interaction element (such as an interaction electrode) is present or is arrangeable, and on a proximal side a contacting element, for example a contacting electrode is arrangeable, with a sealing element sealing off the proximal side from the distal side. The sealing element is such as to allow reversibly contacting the interaction element by the contacting element (in a manner that allows the transmission of the interaction substance or signal). This may be especially by one of the following measures:

The sealing element is a septum element that is pierceable but closes off after removing of the piercing needle; in this the sealing element may be sealingly fastened to the fastening portion, for example by a material connection (weld, adhesive connection, etc.)

The sealing element is a reversibly removable lid that may be sealingly secured to the fastening portion;

The sealing element is a conductor for the signals to be transmitted; especially it may be an electrically conducting membrane. Also in this, the sealing element may be sealingly fastened to the fastening portion, for example by a material connection (weld, adhesive connection, etc.)

The invention further concerns a method of implanting such a device by the described process.

Whereas the described examples with the exception of the one of FIG. 34 show electrodes or electric bridges as interaction elements, it would be readily be possible to use other interaction elements of the kind described in this text.

What is claimed is:

1. A sensing and/or delivery headpiece to be implanted on a human head, the headpiece comprising an array of interaction pins, each interaction pin extending between a proximal end, formed by a proximal end face, and a distal end, and comprising an interaction element and a thermoplastic material,
wherein the interaction element is an electrode;
wherein at least one of the interaction pins further comprises a processor unit communicatively coupled to the interaction element and an antenna communicatively coupled to the processor unit, and is equipped for wireless communication between the processor unit and a further unit;
wherein the processor unit comprises an RFID processor contacting the electrode and being capable of reading out voltage signals picked up by the electrode;
wherein said at least one of the interaction pins comprises a head portion and a shaft portion, the head portion being wider than the shaft portion;
wherein at least the shaft portion comprises the thermoplastic material being arranged at least around a periphery of the shaft portion;
wherein the periphery of the shaft portion comprises a plurality of steps arranged consecutively one distally of the other;
wherein each interaction pin is equipped for the transmission of mechanical vibration energy from the proximal end face to the thermoplastic material to liquefy at least portions of the thermoplastic material from a solid state to a flowable state, whereby the thermoplastic material is capable of flowing into structures of a tissue portion surrounding the periphery and of forming, after re-solidification of the thermoplastic material, an anchoring of the interaction pin in the tissue portion;
wherein the processor unit is equipped to de-couple the antenna from the electrode so that a signal picked up by the antenna does not have any influence on the voltage signals; and
wherein the antenna is located in the head portion.

2. The headpiece according to claim 1, wherein the electrode comprises a proximal interaction electrode and a distal interaction electrode conductively connected to the proximal interaction electrode.

3. The headpiece according to claim 1, wherein a proximal end of the electrode or a distal end of the electrode or both are covered by non-conductive material.

4. The headpiece according to claim 1, wherein the interaction element is arranged to reach to a distal end of the interaction pin, or to not more than 2 mm of the distal end.

5. The headpiece according to claim 1, comprising at least 15 of the interaction pins.

6. The headpiece according to claim 1, wherein at least one of the interaction pins comprises the thermoplastic material so that it is arranged in a manner that in at least one depth it forms the whole surface at least after the liquefaction, so that any functional part is embedded by the thermoplastic material or the thermoplastic material forms a sleeve or collar around any functional parts.

7. The headpiece according to claim 1, wherein the interaction pins are physically separate.

8. The headpiece according to claim 1, wherein at least one of the interaction pins comprises a plurality of spatially separate interaction elements.

9. The headpiece according to claim 1, wherein at least one of the interaction pins is configured to be implanted in a bone tissue around an ear canal.

10. The headpiece according to claim 1, further comprising an interaction device adapted to interact with the interaction elements from outside of the head.

11. The headpiece according to claim 10, wherein the interaction device is reversibly removable.

12. The headpiece according to claim 10, wherein the interaction device is adapted to interact with the interaction elements via skin.

13. The headpiece according to claim 10, wherein the headpiece comprises an array of interaction points, each location of an interaction point corresponding to a location of the interaction element of one of the interaction pins.

14. The headpiece according to claim 10, wherein the interaction device comprises an earpiece shaped to be inserted in an ear canal and interaction points configured to interact with interaction pins implanted in a bone tissue surrounding the ear canal.

\* \* \* \* \*